(12) United States Patent
Meng et al.

(10) Patent No.: US 10,072,097 B2
(45) Date of Patent: Sep. 11, 2018

(54) COMPOSITIONS AND METHODS FOR DETECTION OF PROTEIN S-NITROSYLATION AND OXIDATION

(71) Applicant: ACADEMIA SINICA, Taipei (TW)

(72) Inventors: Tzu-Ching Meng, Taipei (TW); Geen-Dong Chang, Taipei (TW); Ming-Fo Hsu, Taipei (TW)

(73) Assignee: Academia Sinica, Taipei (TW)

( * ) Notice: Subject to any disclaimer, the term of this patent is extended or adjusted under 35 U.S.C. 154(b) by 364 days.

(21) Appl. No.: 14/812,621

(22) Filed: Jul. 29, 2015

(65) Prior Publication Data

US 2016/0033502 A1   Feb. 4, 2016

Related U.S. Application Data

(60) Provisional application No. 62/032,998, filed on Aug. 4, 2014.

(51) Int. Cl.
G01N 33/68 (2006.01)
C07K 16/44 (2006.01)

(52) U.S. Cl.
CPC ......... *C07K 16/44* (2013.01); *G01N 33/6815* (2013.01); *G01N 33/6842* (2013.01); *G01N 2440/26* (2013.01)

(58) Field of Classification Search
CPC .................................. C07K 16/44; G01N 33/68
See application file for complete search history.

(56) References Cited

U.S. PATENT DOCUMENTS 4,123,431 A   10/1978   Soffer et al.
8,053,243 B2   11/2011   Janssen et al.

FOREIGN PATENT DOCUMENTS

EP   1295606 A1   3/2003
EP   1379877 A2   1/2004
WO   2005101019 A2   10/2005

OTHER PUBLICATIONS

Wojdyla et al., "Differential alkylation-based redox proteomics—Lessons learnt", Redox Biology, vol. 6, pp. 240-252, (Year: 2015).*
Hsu et al., "S-nitrosylation of endogenous protein tyrosine phophatases in enothelial insulin signaling," Free Radical Biology and Medicine (2016); 99:199-213.
Hart et al., "Phenacetin Antibody Cross-Reactive With Autoimmune Erythrocyte Antibody," Journal of CLinical Pathology (1969); vol. 52(6):695-701.
Forrester et al., "Detection of protein S-nitrosylation with the biotin-switch technique," Free Radical Biology & Medicine (2009); 46:119-126.
Chen et al., "Cysteine S. Nitrosylation Protects Protein-tyrosine Phosphatase 1B against Oxidation-induced Permanent Inactivation," The Journal of Biological Chemistry (2008); 283(50):35265-35272.
Jaffrey et al., "Protein S-nitrosylation: a physiological signal for neuronal nitric oxide," Nature Cell Biology (Feb. 2001), vol. 3:193-197.

* cited by examiner

*Primary Examiner* — Tracy Vivlemore
*Assistant Examiner* — Nam P Nguyen
(74) *Attorney, Agent, or Firm* — Fox Rothschild LLP

(57) ABSTRACT

The present invention discloses a novel isolated antibody that specifically binds to an N-phenyl-acetamide group. Also disclosed are related compositions, kits, methods for detecting protein S-nitrosylation or oxidation vivo or in vitro, and drug screening methods.

7 Claims, 7 Drawing Sheets

Specification includes a Sequence Listing.

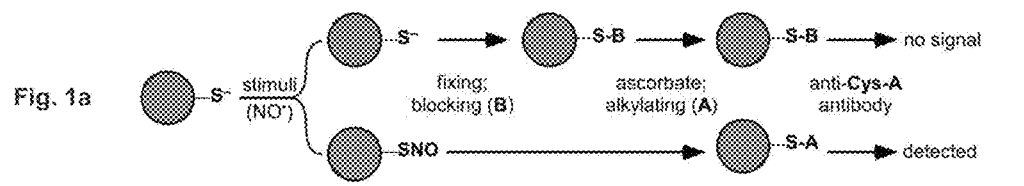
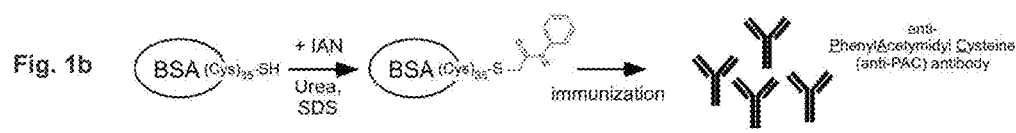
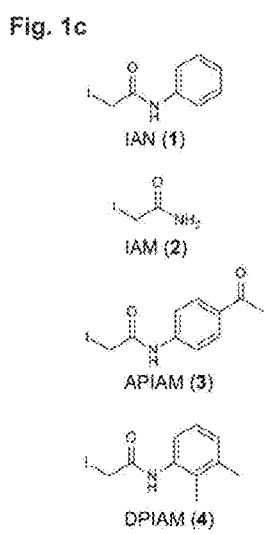
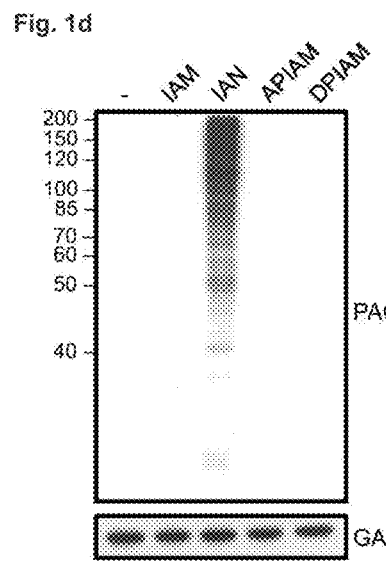
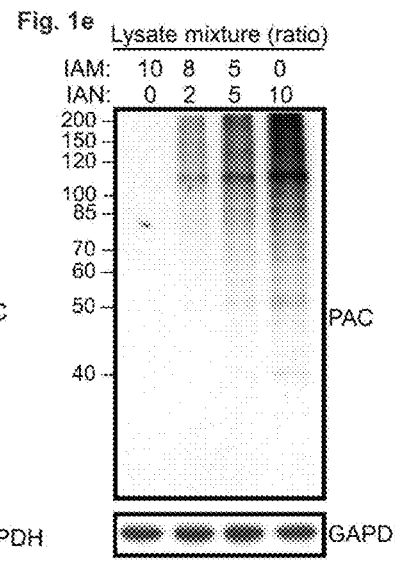
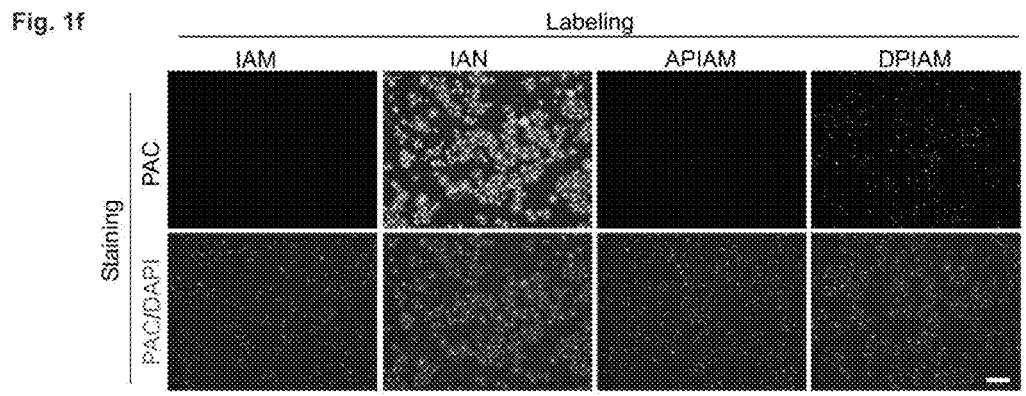

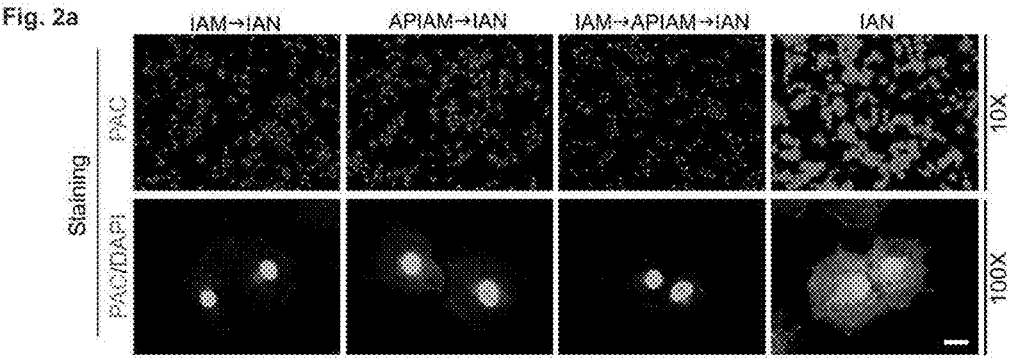
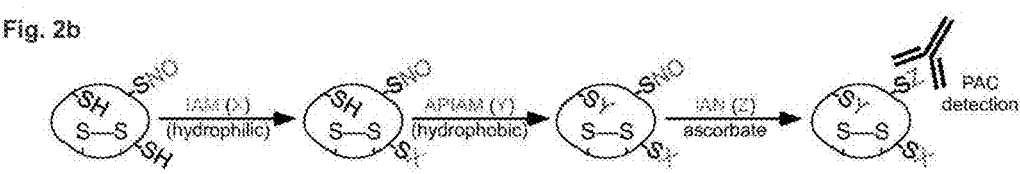
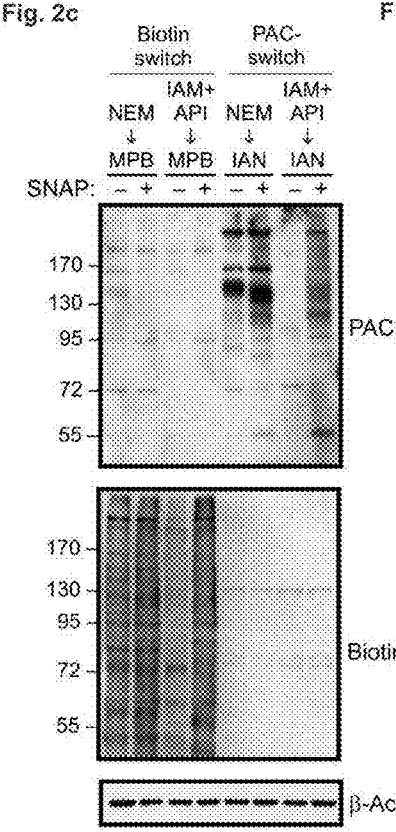
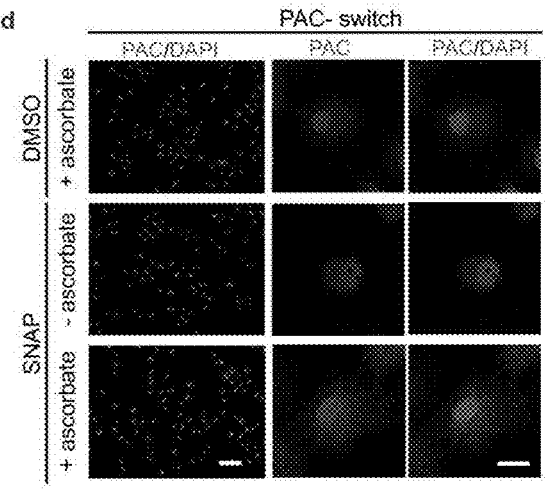
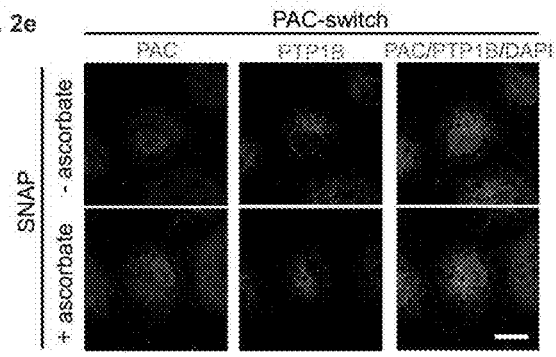

COMPOSITIONS AND METHODS FOR DETECTION OF PROTEIN S-NITROSYLATION AND OXIDATION

CROSS REFERENCE TO RELATED APPLICATION

This application claims priority to U.S. Provisional Application No. 62/032,998 filed on Aug. 4, 2014. The content of the application is incorporated herein by reference in its entirety.

BACKGROUND OF THE INVENTION

Nitric oxide (NO), which can be produced intracellularly by endogenous NO synthase (NOS), acts as an important second messenger. The known functions of NO include regulation of smooth muscle relaxation, platelet aggregation, neurotransmission, neurotoxicity, cell death and differentiation. In order to promote smooth muscle relaxation in vasculature, NO targets the heme group located at the active-site of soluble guanylyl cyclase, resulting in elevation of its enzymatic activity, consequently leading to vasorelaxation.

For executing other biological functions, NO is likely to react with cysteine (Cys) residues in proteins. The reaction of NO with cysteine residues in proteins to form S-nitrosothiol (SNO) is a post-translational modification process known as protein nitrosation or S-nitrosylation. Protein S-nitrosylation regulates the activity of a large number of targets, including metabolic, structural, cytoskeletal, and signaling proteins, and is an important mechanism for nitric oxide signaling.

Although significant progress has been made to understand the biological function of protein S-nitrosylation, the role of nitrosylation in regulating signal transduction has not been well characterized. The detection of protein S-nitrosylation in complex biological system remains challenging due to technical limitations of current methods, and the unstable nature of S—N bonds in S-nitrosothiols (SNO).

Current methods known in the arts for the detection of SNO include indirect detection methods and direct detection methods. An immunohistochemical approach using anti-S-nitrosocysteine antibody is a direct method for detection of protein S-nitrosylation. Yet, as the unstable S—N bonds may be broken during SDS-PAGE separation in immunoprecipitation or Western blotting, the method is not typically performed. Indirect methods usually break the unstable S—N bonds and capture either the sulfur or the nitrogen part for detection. Among methods for studying protein S-nitrosylation, the biotin switch method (Jeffery (2001) Nat Cell Biol, 3: 193-197) has become a mainstay assay due to the ease with which it can detect individual S-nitrosylated (SNO) proteins in biological samples. Expression of endogenous biotin in various tissues including kidney, liver and brain has been well documented in literatures (Wang (1999) Cell Tissue Res, 296: 511-516; McKay (2004) J Comparative Neurology, 473: 86-96). It was also shown that mitochondrial matrix contains a significant level of biotinylated proteins (Hollinshead (1997) J Histochem Cytochem, 45: 1053-1057). The presence of endogenous biotin and biotinylated proteins may cause unexpected background signals in any application of biotin-avidin or biotin-streptavidin technique, including the biotin-switch method. The problems caused by endogenous biotin and biotinylated proteins suggest that many false-positive results have been generated by the biotin-switch method since its introduction 15 years ago.

Insulin delivery to the skeletal muscle interstitium plays a key role in insulin-directed glucose uptake by skeletal muscle. This insulin signaling-dependent process is tightly controlled by the endothelial barrier function of the capillaries connected to skeletal muscle. It has been shown that intrinsic NO functions to promote insulin delivery across endothelial barrier. However, to date the mechanism underlying NO-dependent insulin responsiveness in endothelium remains uncharacterized due to technical limitations of current detection methods for protein S-nitrosylation.

Thus, there remains an unmet need in the art for a new analytic platform to enhance the specificity and accuracy of the detection of S-nitrosylated proteins and facilitate the study of S-nitrosylation's role in signal transduction pathways.

SUMMARY OF THE INVENTION

The present invention provides an isolated antibody as well as compositions and methods for detection of protein S-nitrosylation specifically in vivo and in vitro. The methods of the invention can eliminate false-positive detection of S-nitrosylated protein, and enable the monitoring of the subcellular localization of S-nitrosylated proteins in cells. The methods of the invention can facilitate the understanding of the molecular mechanism of S-nitrosylation's role in signal transduction pathways. This invention also provides the application of detection in both biochemical and cell imaging formats.

Accordingly, the present invention relates to an isolated antibody that specifically binds to a moiety having the structure of formula (A):

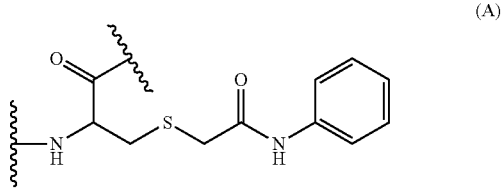 [SMILES: *NC(CSCC(=O)Nc1ccccc1)C(*)=O]

(A)

The antibody of the invention specifically targets N-phenyl-acetamide group, and does not cross react with the moieties of formulae (B), (C) and (D):

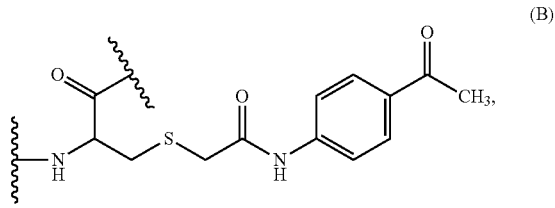

(B)

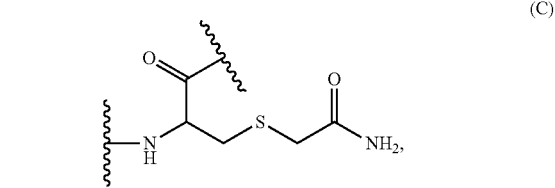

(C)

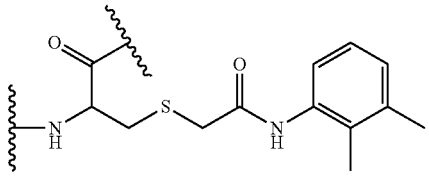
(D)

The isolated antibody disclosed herein is useful for detecting protein nitrosylation and oxidation in a protein substrate, which includes, but is not limited to, cells and tissues.

Another aspect of the invention provides a method for determining the presence or absence of protein S-nitrosylation and/or oxidation in vivo and in vitro.

The inventive method for determining the presence or absence of protein S-nitrosylation or oxidation comprises the following steps: a) contacting a sample with one or more reducing agents, b) treating the sample with a thiol-reactive probe to form one or more N-phenyl-acetamidyl cysteines, and c) detecting the N-phenyl-acetamidyl cysteine or cysteines by an anti-N-phenyl-acetamidyl cysteine (PAC) antibody, thereby determining the presence or absence of protein S-nitrosylation or oxidation.

In some embodiments, the method further comprises a step of blocking all sulfhydryl (SH) groups of reduced cysteine residues in the sample prior to step (a). The step of blocking SH groups can be performed by one or more sulfhydryl-reactive alkylating agents that selectively react with sulfhydryl (SH) groups. Preferably, the sulfhydryl-reactive alkylating agents are haloacetyl reagents. In some embodiments, alkylating agents are iodoacetyl or bromoacetyl reagents. In specific embodiments, the alkylating agents are iodoacetyl reagents. More preferably, the alkylating agents comprise iodoacetamide (IAM), N-(4-acetyl-phenyl)-2-iodoacetamide (APIAM) and/or N-(2,3-dimethyl-phenyl)-2-iodoacetamide (DPIAM). In some examples, the sample is treated with IAM and APIAM sequentially or simultaneously. These sulfhydryl-reactive alkylating agents react with sulfhydryl (SH) groups of cysteine residues at physiologic to alkaline conditions (pH 7.2 to 9) to form stable thioether linkages.

In a preferred embodiment, step a) in the method is to convert S-nitrosothiol (SNO) moiety and/or disulfide moiety to sulfhydryl (SH) moiety by using one or more reducing agents.

In some examples, the reducing agent is a disulfide reducing agent. The disulfide reducing agent includes, but not limited to, Tris-(2-carboxyethyl)phosphine (TCEP), Tris-(hydroxypropyl)phosphine (THP), Dithiothreitol (DTT), Tris(3-hydroxypropyl)phosphine (THPP), cysteine, glutathione or combinations thereof.

In some examples, the reducing agent is an ascorbate or ascorbic acid. Ascorbate is a physiological antioxidant that serves as a SNO-specific reducing agent. After ascorbate treatment, S-nitrosothiols release NO on decomposition.

After treatment with one or more reducing agents, one or more nitrosothiols and/or one or more disulfides in the sample are converted to one or more sulfhydryls. The newly generated sulfhydryl can react with a thiol-reactive alkylating agent, 2-Iodo-N-phenylacetamide (IAN), to form stable N-phenyl-acetamidyl cysteine as described in step (b). N-phenyl-acetamidyl cysteine can be specifically targeted by the antibody of the invention, anti-N-phenyl-acetamidyl cysteine (PAC) antibody, thereby determining the presence or absence of protein S-nitrosylation or oxidation as described in step (c).

Any detectable label may be used with the antibody of the invention, such as fluorescent labels, radiolabels, enzymatic labels, and others. In particular embodiments, the detectable label is an optically-detectable label, such as a fluorescent label. Exemplary fluorescent labels include Atto, cyanine, rhodamine, fluorescien, coumarin, BODIPY, alexa, and conjugated multi-dyes.

The inventive method can both quantify and identify the nature of nitrosylated and/or oxidative proteins, and can be used for screening therapeutic drugs that potentially modulating protein nitrosylation or oxidation.

In yet another aspect, this invention is directed to a kit suitable for performing an assay which determines the presence or absence of protein S-nitrosylation and/or oxidation. The kit of this invention comprises the components referred to in the methods described above. In some embodiments, the kit of the invention comprises the antibody of the invention described herein. In some embodiments, the kit comprises the antibody of the invention and 2-iodo-N-phenyl-acetamide (IAN). In some embodiments, the kit further comprises sulfhydryl-reactive alkylating agents comprising IAM, APIAM and/or DPIAM. In certain embodiments, the kit may contain ascorbate and/or ascorbic acid. In certain embodiments, the kit further comprises one or more disulfide alkylating agents and/or at least one reducing agent selecting from the group consisting of TCEP, THP, DTT, THPP, cysteine, glutathione, and combinations thereof. In some cases, a kit of this invention comprises all components described above, instructions setting forth a procedure according to any one of the methods described above, and a container for the contents of the kit.

In some cases, the present invention relates to visualization techniques for in situ imaging of nitrosylated and/or oxidized proteins within cells and/or tissues. The method for detecting a nitrosylated and/or oxidized protein in situ comprises the step of a) contacting a sample with one or more reducing agents, (b) reacting the sample with N-phenyl-acetamide to form N-phenyl-acetamidyl cysteines, and c) detecting N-phenyl-acetamidyl cysteines by an anti-N-phenyl-acetamidyl cysteine (PAC) antibody, thereby detecting the nitrosylated and/or oxidized protein.

This invention also provides an analytic platform derived from the method for screening for drugs that potentially modulate protein nitrosylation or oxidation. This analytic platform is useful for both in vitro and in vivo conditions.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

FIG. 1a, FIG. 1b, FIG. 1c, FIG. 1d, FIG. 1e, and FIG. 1f: Generation of anti-PAC antibody and validation of its performance. (FIG. 1a) A workflow to detect S-nitrosylated proteins by an anti-Cys-A antibody. (FIG. 1b) To materialize anti-Cys-A antibody that could be applied in the workflow shown in FIG. 1a, the procedure was designed to generate anti-phenylacetymidyl-cysteine (anti-PAC) antibody using BSA as a carrier protein. (FIG. 1c) Four synthetic alkylating reagents for the specificity test of anti-PAC antibody. (FIG. 1d) An aliquot of total lysates from COS-7 cells was reacted with IAM, IAN, APIAM or DPIAM, and then subjected to immunoblotting with anti-PAC antibody. (FIG. 1e) Aliquots of IAN- and IAM-reacted total lysates from COS-7 cells were mixed following the ratio shown in the figure. Subsequently samples were subjected to immunoblotting with anti-PAC antibody. (FIG. 1f) COS-7 cells were fixed, permeabilized and then exposed to IAM, IAN, APIAM or DPIAM. After washes, anti-PAC antibody was added for visualization of cellular proteins with Cys tagged by alkylation reagents.

FIG. 2a, FIG. 2b, FIG. 2c, FIG. 2d, and FIG. 2e: Development and validation of the PAC-switch method for detection of S-nitrosylated proteins. (FIG. 2a) Fixed and permeabilized COS-7 cells were sequentially treated with one or two blocking reagents before finally exposed to IAN as shown in the figure. After washes, anti-PAC antibody was added for visualization of cellular proteins with Cys tagged by IAN. Nucleus was stained with DAPI. (FIG. 2b) The procedure of the PAC-switch method to detect S-nitrosylated proteins was developed. Free thiols are blocked by sequential addition of IAM (-SX) and APIAM (-SY). S-nitrosylated Cys is reduced by ascorbate, tagged by IAN (-SZ), and then detected by anti-PAC antibody. (FIG. 2c) Comparison between the Biotin-switch method and the PAC-switch method for detection of S-nitrosylated proteins. Unstimulated or SNAP-treated COS-7 cells were lysed in the presence of NEM for blocking of free thiols, followed by addition of ascorbate together with MPB or IAN for tagging originally S-nitrosylated proteins. Alternatively, total lysates were sequentially reacted with IAM and APIAM (API) for blocking of free thiols, followed by addition of ascorbate and MPB or IAN for tagging originally S-nitrosylated proteins. Aliquots of total lysates were subjected to immunoblotting with either anti-PAC antibody or anti-Bioin antibody. (FIG. 2d and FIG. 2e) SNAP-treated COS-7 cells were fixed, permeabilized and then processed by the PAC-switch method. (FIG. 2d) S-nitrosylated proteins were visualized by anti-PAC antibody. (FIG. 2e) Cells were co-stained with anti-PAC antibody and anti-PTP1B antibody. (FIG. 2d and FIG. 2e) Nucleus was stained with DAPI.

(FIG. 3a) Mouse MS-1 endothelium was exposed to insulin for indicated times. Aliquots of total lysates were subjected to immunoblotting with anti-pYpY$^{1162/1163}$-insulin receptor β-subunit (InRβ), anti-InRβ, anti-pS$^{1177}$-eNOS, and anti-eNOS antibodies. (FIG. 3b) MS-1 cells electroporated with scramble siRNA oligonucleotides or siRNA oligonucleotides to eNOS were exposed to insulin for 5 or 10 min. Aliquots of total lysates were subjected to immunoblotting with indicated antibodies. FIG. 3c and FIG. 3d) MS-1 cells exposed to insulin for 5 and 30 min were lysed and processed by the PAC-switch method. (FIG. 3c) Aliquots of total lysates (input) or processed lysates (PAC-switch) were subjected to immunoblotting with anti-PAC antibody. (FIG. 3d) An aliquot of processed lysates was subjected to immunoprecipitation with anti-PTP1B antibody. After washes, immunocomplexes were analyzed by immunoblotting with anti-PAC and anti-PTP1B antibodies (upper panel). Results of densitometric analysis of the gel images as a ratio of PAC intensity relative to total PTP1B from three independent experiments were shown in the lower panel (*, p<0.01; NS, not significant).

(FIG. 4a) MS-1 cells treated with insulin for indicated times were fixed, permeabilized and stained with anti-PTP1B and anti-pS$^{1177}$-eNOS (peNOS) antibodies. A pool of PTP1B translocated to the cell periphery was co-localized with peNOS in cells exposed to insulin for 5 min (white arrowheads). (FIG. 4b) MS-1 cells treated with insulin were fixed, permeabilized and processed by the PAC-switch method. Subsequently cells were stained with anti-PTP1B and anti-PAC antibodies. A pool of PTP1B translocated to the cell periphery was co-stained with anti-PAC antibody (white arrowheads), suggesting its S-nitrosylation in cells exposed to insulin for 5 min. Enlarged view (images extracted from boxes) shows the colocalization of (FIG. 4a) PTP1B and peNOS, or (FIG. 4b) PTP1B and PAC signal, to the cell boundary in response to insulin stimulation.

(FIG. 5a) MS-1 cells treated with insulin for 5 min were fixed, permeabilized and stained with PTP1B and anti-pYpY$^{1162/1163}$-insulin receptor β-subunit (pInRβ) antibodies. A pool of PTP1B translocated to the cell periphery was co-localized with activated IR in cells exposed to insulin (white arrowheads). (FIG. 5b) MS-1 cells treated with insulin were processed as described in FIG. 5a. For visualizing colocalization between PTP1B and pInRβ, the proximity ligation assay (PLA) was performed. Signals shown in red fluorescence indicate that a pool of PTP1B translocated to cell periphery was within 40 nm from pInRβ (white arrowheads). (FIG. 5c) MS-1 cells electroporated with scramble siRNA oligonucleotides or siRNA oligonucleotides to eNOS were exposed to insulin for 5 min. After fixing, cells were processed by the PAC-switch method, and subsequently stained with indicated antibodies. A pool of PTP1B translocated to the cell periphery was co-stained with anti-PAC and anti-pInRβ antibodies (white arrowheads), suggesting colocalization between S-nitrosylated PTP1B and activated IR along the cell boundary in response to insulin stimulation. This event was abolished when eNOS was ablated by RNAi.

(FIG. 6a) eNOS-ablated MS-1 cells were transfected with either an empty vector or a vector expressing HA-tagged C215S mutant form of PTP1B (HA-C/S-PTP1B). Transfectants treated with insulin for 5 min were fixed, permeabilized and then stained with anti-HA and anti-pYpY$^{1162/1163}$-insulin receptor β-subunit (pInRβ) antibodies. A pool of HA-C/S-PTP1B translocated to the cell periphery was co-stained with anti-pInRβ antibody (white arrowheads) in response to insulin stimulation. (FIG. 6b) MS-1 control cells and transfectants as described in FIG. 6a were treated with insulin for 5 min. Aliquots of total lysates were subjected to immunoblotting with indicated antibodies (left panel). The right panel shows a denstometric analysis of the gel image from three independent experiments as a ratio of phosphorylated InRβ relative to total InRβ.

DETAILED DESCRIPTION OF THE INVENTION

Figure 3A:
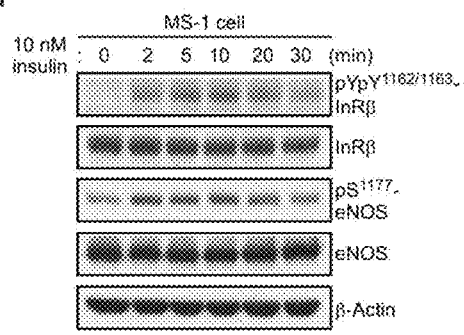
FIG. 3a, FIG. 3b, FIG. 3c, and FIG. 3d: Insulin stimulation-dependent PTP1B S-nitrosylation in endothelium derived from capillary.

The invention provides a new antibody-based method to detect S-nitrosylated and/or oxidized proteins with high specificity and accuracy. The antibody-based strategy is illustrated in FIG. 1a. The proteins that are recognized by the antibody of the invention can be those originally protected from post-fixing blocking (B) by a stimulus-dependent modification at the susceptible Cys, which can be reversed by reducing agents such as ascorbate then being alkylated (A), consistent with S-nitrosylation of the Cys. The success of such strategy relies on the specificity of the novel antibody which specifically targets the alkylated Cys after ascorbate-mediated reduction, but does not react with the fraction of Cys residues being blocked or any endogenous biomolecules present in cells.

As used herein, S-nitrosoproteins, S-nitrosothiols, and protein S-nitrosylation reactions are terms that refer to components with linkage through the thiol (—SH) group. These types of components play important roles in cell signaling processes such as neurotransmission, anion channel regulation, host defense and gene regulation.

As used herein, the term "alkylating agent" or "sulfhydryl-reactive alkylating agent" refers to an agent that forms alkylthiol groups when reacted under suitable conditions with free thiol groups. Alkylating agents contain straight or branched chain lower alkyl (C1-C6) groups that may be derivatized or functionalized. Generally, a blocking agent can be used to block free thiols in the test sample when carrying out the method of this invention. The blocking agent is preferably removed from the test sample prior to step (a) of the method of this invention.

Unless indicated otherwise by context, by "sample" or "test sample" is meant any sample which may be suitably tested using the methods disclosed herein. Test samples can be e.g. in the form of any biological sample, for example, crude, purified or semipurified lysates of tissues that potentially comprise nitrosylated proteins, e.g. brain, peripheral nerve, muscle, blood vessels, blood cells, liver, etc.

As used herein, the term "reducing agent" refers to a compound such as ascorbate that reduces nitrosothiol bonds on a protein to form new free thiol groups. Agents such as $Cu^{2+}$ or $Hg^{2+}$ may also be used. Care must be taken to remove these, as these metals can interfere with antibody incubation and detection.

The present invention provides an isolated antibody useful for in situ imaging of S-nitrosylated proteins in cells with high specificity and accuracy. The invention also provides an antibody-based method illustrated in FIG. 1 to detect S-nitrosylated proteins with high specificity and accuracy.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. As used herein, the terms also mean that binding between two entities has an affinity as quantified by an association constant, K, of at least $10^6$ $M^{-1}$, $10^7$ $M^{-1}$, $10^8$ $M^{-1}$, $10^9$ $M^{-1}$, or $10^{10}$ $M^{-1}$.

Anti-PAC Antibody

The present invention provides an isolated antibody useful for in situ imaging of S-nitrosylated proteins in cells with high specificity and accuracy. The antibody described herein can be either monoclonal or polyclonal. A "monoclonal antibody" refers to a homogenous antibody population and a "polyclonal antibody" refers to a heterogenous antibody population.

Antibodies described herein can be made by any method known in the art. See, for example, Harlow and Lane, (1988) Antibodies: A Laboratory Manual, Cold Spring Harbor Laboratory, New York.

Polyclonal antibodies may be prepared by collecting blood from an immunized mammal examined for the increase of desired antibodies in the serum, and by separating serum from the blood using any conventional method. Polyclonal antibodies include serum containing the polyclonal antibodies, as well as a fraction containing the polyclonal antibodies that may be isolated from the serum.

Polyclonal antibodies are generally raised in host animals (e.g., rabbit, mouse, guinea pig, horse, or goat) by multiple subcutaneous (sc) or intraperitoneal (ip) injections of a relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, etc.

Any mammalian animal may be immunized with the antigen for producing the desired antibodies. In general, animals of Rodentia, Lagomorpha, or Primates can be used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Animals can be immunized with the antigen, immunogenic conjugates, or derivatives by combining 1 mg or 1 μg of the antigen or conjugate (for rabbits or mice, respectively) with 3 volumes of Freund's incomplete adjuvant.

Animals can be boosted until the titer plateaus by several administrations of antigen mixed with an appropriately amount of Freund's incomplete adjuvant every 4 to 21 days. Animals are boosted with ⅕ to 1/10 the original amount of antigen or conjugate in Freund's complete adjuvant by subcutaneous injection at multiple sites. Seven to 14 days later the animals are bled and the serum is assayed for antibody titer. An appropriate carrier may also be used for immunization. After immunization as above, serum is examined by a standard method for an increase in the amount of desired antibodies. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Over the past two to three decades, a number of methodologies have been developed to prepare chimeric, humanized or human antibodies for human in-vivo therapeutic applications. The most used and proven methodology is to prepare mouse mAbs using hybridoma methodology and then to humanize the mAbs by converting the framework regions of the $V_H$ and $V_L$ domains and constant domains of the mAbs into most homologous human framework regions of human $V_H$ and $V_L$ domains and constant regions of a desirable human γ immunoglobulin isotype and subclass.

Many mAbs, such as Xolair, used clinically are humanized mAbs of human γ1, κ isotype and subclass and prepared using this methodology.

In some embodiments, antibodies can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that will specifically bind to the antigen used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma, to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used in this method. BIAcore (Pharmacia) may be used to evaluate the activity of the antibody according to the present invention. The binding affinity of the monoclonal antibody can, for example, be determined by the Scatchard analysis of Munson et al., Anal. Biochem., 107:220 (1980).

Applying any of the conventional methods, including those described above, hybridoma cells producing antibodies that bind to epitopes described herein can be identified and selected for further characterization.

After hybridoma cells that produce antibodies of the desired specificity, affinity, and/or activity are identified, the corresponding clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In addition, the hybridoma cells may be grown in vivo as ascites tumors in an animal. For example, the obtained hybridomas can be subsequently transplanted into the abdominal cavity of a mouse and the ascites are harvested.

The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention.

Applications of PAC-Switch Method
(i) Method for Detecting S-nitrosylation or Cys Oxidation of Proteins The invention provides a method for determining the presence or absence of S-nitrosylation or reversible Cys oxidation of protein substrates in vivo and in vitro. The method for assaying nitrosylation of protein substrates is described herein. This antibody together with the inventive method can also be used for assaying reversible Cys oxidation of protein substrates.

The inventive method for determining the presence or absence of protein S-nitrosylation or oxidation comprises the following steps: a) contacting a sample with one or more reducing agents, b) treating the sample with a thiol-reactive probe to form N-phenyl-acetamidyl cysteine, and c) detecting N-phenyl-acetamidyl cysteine by an anti-N-phenyl-ac-etamidyl cysteine (PAC) antibody, thereby determining the presence or absence of protein S-nitrosylation or oxidation.

In some cases, unmodified thiol moieties are present within the protein and/or proximate proteins near the protein suspected of being nitrosylated (or otherwise oxidized). In tht cases, the unmodified (i.e., non-nitrosylated) thiol moieties may be initially blocked or otherwise altered before the nitrosothiol moiety is converted into an alkylthio moiety, such that the unmodified thiol moieties are not able to react in the same fashion as the nitrosothiol moieties. Any suitable techniques for blocking unmodified thiol groups on a protein from reaction may be used. For example, thiol moieties on the protein may first be converted to alkylthio moieties, prior to reaction of the nitrosothiol moieties with reducing agent and IAN to form alkylthio moieties. As a non-limiting example, unmodified thiol moieties on a protein may be reacted with thiol-reactive alkylating agents that are halo-acetyl reagents. In some embodiments, alkylating agents are iodoacetyl or bromoacetyl reagents. In specific embodiments, the alkylating agents are iodoacetyl reagents. In some embodiments, the alkylating agent includes an iodoacet-amide moiety or an iodoacetate moiety, for example, as in 2-iodoacetamide or 2-iodoacetate.

Preferably, the alkylating agents comprise iodoacetamide (IAM), N-(4-acetylphenyl)-2-iodoacetamide (APIAM) and/or N-(2,3-dimethylphenyl)-2-iodoacetamide (DPIAM). In one example, a test sample comprising at least one protein substrate is treated with two alkylating reagents (e.g. IAM and APIAM) sequentially. In some examples, a test sample comprising at least one protein substrate is treated with two alkylating reagents (e.g. IAM and APIAM) simultaneously. These sulfhydryl-reactive alkylating agents react with sulf-hydryl (SH) groups of cysteine residues at physiologic to alkaline conditions (pH 7.2 to 9) to form stable thioether linkages.

For assaying oxidation, reversibly oxidized Cys bonds or disulfide bonds on the protein substrates are reduced by disulfide reducing agents to form free thiol groups. Disulfide reducing agents include, but not limited to, Tris-(2-carboxy-ethyl)phosphine (TCEP), Tris-(hydroxypropyl)phosphine (THP), Dithiothreitol (DTT), Tris(3-hydroxypropyl)phos-phine (THPP), cysteine, glutathione, and combinations thereof.

For assaying nitrosylation, nitrosothiol bonds on the pro-tein substrates are reduced by ascorbate to form free thiol groups. In some examples, the reducing agent is an ascor-bate or ascorbic acid. Ascorbate is a physiological antioxi-dant that serves as a SNO-specific reducing agent. After ascorbate treatment, S-nitrosothiols release NO on decom-position.

The newly generated sulfhydryl can react with a thiol-reactive probe, 2-iodo-N-phenyl-acetamide, to form stable N-phenyl-acetamidyl cysteine as described in step (b). N-phenyl-acetamidyl cysteine can be specifically targeted by the antibody of the invention, anti-N-phenyl-acetamidyl cysteine (PAC) antibody, thereby determining the presence or absence of protein S-nitrosylation or oxidation as described in step (c).

Any detectable label may be used with the antibody of the invention, such as fluorescent labels, radiolabels, enzymatic labels, and others. In particular embodiments, the detectable label is an optically-detectable label, such as a fluorescent label. Exemplary fluorescent labels include Atto, cyanine, rhodamine, fluorescien, coumarin, BODIPY, alexa, and con-jugated multi-dyes.

Scheme 1 illustrates the steps (a) and (b) in the inventive method described above. Route (IA) shows the conversion of S-nitrosothiol (SNO) to sulfhydryl (SH) by reducing agents such as an ascorbate or ascorbic acid. Route (IB) shows the conversion of disulfide to sulfhydryl. Route (II) shows the formation of N-phenyl-acetamidyl cysteine.

Scheme 1:

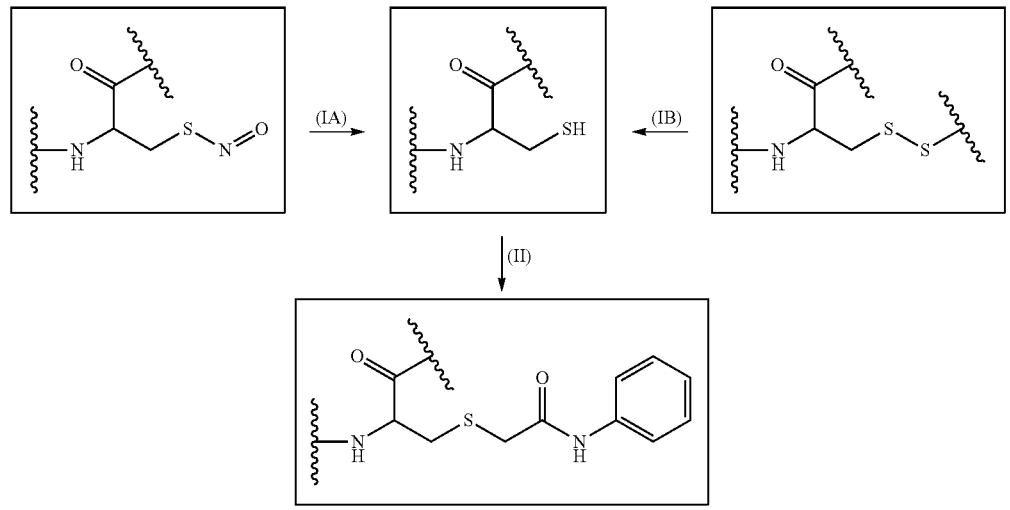

In a preferred embodiment, step a) in the method is to convert S-nitrosothiol (SNO) moiety and/or disulfide moiety to sulfhydryl (SH) moiety by one or more reducing agents. In some examples, the reducing agent is an ascorbate or ascorbic acid.

The invention, in another aspect, may be used to deter-mine a characteristic of a protein in vivo or in vitro. In some embodiments, a protein may be detected in vitro or in isolation, e.g., within a protein assay, for example, within a 96-well plate or other microwell plate. For instance, an embodiment of the invention may be used to determine oxidized proteins such as nitrosylated proteins in a sample, e.g., a synthetically prepared sample, a sample from cell culture or tissue culture, a cell lysate, and/or a sample from a subject, such as a human, a non-human primate, a cow, a horse, a pig, a sheep, a goat, a dog, a cat or a rodent such as a mouse, a rat, a hamster, a guinea pig, etc. A "sample," as used herein, is any cell, body tissue, or body fluid sample obtained from a subject. Examples of body fluids include lymph, saliva, blood, urine, and the like. Samples of tissue and/or cells for use in the various methods described herein can be obtained through standard methods including, but not limited to, tissue biopsy, including punch biopsy and cell scraping, needle biopsy, collection of blood or other bodily fluids by aspiration, or other suitable methods.

In some embodiments, oxidized proteins such as nitrosylated proteins may be determined in an intact cell. The intact cell may be alive, or the intact cell may be fixed in some cases. Determination of the protein in the cell may include determining the presence or absence of the proteins within the cell, determining the concentration of the proteins within the cell, and/or determining the location of the proteins within the cell, e.g., within organelles within the cell, such as within the nucleus, within mitochondria, within lysosomes, etc.

In some embodiments, oxidized proteins such as nitrosylated proteins may be determined within tissue, for example, brain tissue, lung tissue, etc. In some embodiments, such determination of the nitrosylated and/or other oxidized proteins within the tissue allows the spatial locations and/or concentrations of the proteins within the tissues to be identified and/or measured, for example, quantitatively. The tissue may be alive, or fixed in some cases. Determination of the oxidized proteins may include determining the amount of protein present, and/or determining the spatial location of the oxidized proteins within the tissue, or within portions of the tissue (e.g., within certain structures comprising the tissue, within certain cells within the tissue, within certain regions of cells within the tissue, etc.). Thus, as a non-limiting example, a reaction where nitrosylated proteins become fluorescent may be used, according to the invention, to resolve the location of nitrosylated proteins within a tissue sample, such as within lung tissue. In still another set of embodiments, the invention provides for the determination of oxidized proteins, such as nitrosylated proteins, within a subject.

There are unique features that make this PAC-switch method superior to those existing analytic platforms, including the widely used biotin switch method (European patent EP1379877B1; Jeffery (2001) Nat Cell Biol, 3: 193-197), which were developed by others for the same purpose. These unique features include:

(1) The application of this invention can eliminate false-positive results caused by free thiols. The inventors validated the strategy of the PAC-switch method by treating COS-7 cells with NO donor S-nitroso-N-acetylpenicillamine (SNAP). Following the protocol shown in FIG. 2b, the inventors subjected processed lysates to immunoblotting with anti-PAC antibody. In the absence of SNAP, the PAC signal was barely detected in total lysates, indicating successful blocking of free thiols by the alkylating reactions with IAM and APIAM. On the other hand, the treatment of SNAP led to significant increases of the PAC signal in a broad range of cellular proteins. These results suggested that stimulus-induced S-nitrosylation of endogenous proteins can be detected reliably by this method. For comparison, the inventors also tested the effect of N-ethylmaleimide (NEM), which was recommended by Jeffery et al. for the published biotin-switch method to prevent false-positive signal, on blocking of free thiols in the context of SNAP-induced S-nitrosylation of cellular proteins. The results showed that NEM was unable to eliminate the PAC signal derived from untreated cells. Even though the stimulation of cells with SNAP led to a small degree of increased PAC signals, incomplete blocking of free thiols by NEM rendered visualization of S-nitrosylated proteins questionable under such circumstance.

(2) The use of anti-PAC antibody rather than avidin or streptavidin-based detection for S-nitrosothiols can prevent false-positive results due to the interference of endogenous biotin and biotinylated proteins. Expression of endogenous biotin in various tissues including kidney, liver and brain has been well documented in literatures (Wang (1999) Cell Tissue Res, 296: 511-516; McKay (2004) J Comparative Neurology, 473: 86-96). It was also shown that mitochondrial matrix contains a significant level of biotinylated proteins (Hollinshead (1997) J Histochem Cytochem, 45: 1053-1057). The presence of endogenous biotin and biotinylated proteins may cause unexpected background signals in any application of biotin-avidin or biotin-streptavidin technique, including the biotin-switch method. The problems caused by endogenous biotin and biotinylated proteins suggest that many false-positive results have been generated by the biotin-switch method since its introduction 15 years ago. Therefore, it is proposed herein that published studies using biotin-avidin or biotin-streptavidin-based detection for protein S-nitrosylation should be critically reevaluated by the PAC-switch method, which significantly alleviates the chance of false-positive results.

(ii) Screening of Potential Drugs that Modulate Protein Nitrosylation and Oxidation The inventive method can both quantify and identify the nature of nitrosylated and/or oxidative proteins, and can be used in screening for therapeutic drugs that modulate protein nitrosylation or oxidation.

In some examples, a test sample comprising at least one protein substrate is exposed to a drug of interest. The test sample is treated with one or more alkylating reagents; for examples, two alkylating reagents such as IAM and APIAM are used sequentially or simultaneously. This step blocks free thiol groups on the protein substrates or other irrelevant proteins present in the test sample.

For assaying nitrosylation, nitrosothiol bonds on the protein substrates can be reduced by ascorbate to form free thiol groups. For assaying oxidation, reversibly oxidized Cys bonds or disulfide bonds on the protein substrates can be reduced by DTT or TCEP to form free thiol groups. Free thiol groups on the protein substrate can be reacted with alkylating reagent IAN to form a detectable tag phenylacetamidyl Cys. The detectable tag on the protein substrates can be detected by anti-PAC antibody, which recognizes phenylacetamidyl Cys specifically. Level of N-phenylacetamidyl Cys on the protein substrate of the test sample can be compared to a level in a control sample with identical treatment but is not exposed to the drug of interest. The drug with the potential to either increase or decrease protein nitrosylation or oxidation can be identified by the level of phenylacetamidyl Cys in the test sample relative to the control sample.

Kits

This invention also provides a kit suitable for performing an assay which detects the presence of protein S-nitrosylation. Preferably, the kit provides the capability of detecting the nitrosylated and/or oxidative proteins and identifying the nitrosylated and/or oxidative proteins in a sample. Also, preferably, the kit provides the capability of quantifying the amount of nitrosylated and/or oxidative species in a biological sample using the kit.

The kit of this invention comprises one or more of the components referred to in the methods described above. In some embodiments, the kit of the invention comprises the antibody of the invention described herein. In some embodiments, the kit comprises the antibody of the invention and 2-iodo-N-phenyl-acetamide (IAN). In some embodiments, the kit further comprises sulfhydryl-reactive alkylating agents comprising IAM, APIAM and/or DPIAM. In certain embodiments, the kit may contain ascorbate and/or ascorbic acid. In certain embodiments, the kit further comprises one or more disulfide alkylating agents and/or at least one reducing agent selecting from TCEP, THP, DTT, THPP, cysteine, glutathione or combinations thereof. In some cases, the kit of this invention comprises all components described above, instructions setting forth a procedure according to any one of the methods described above and a container for the contents of the kit. In some cases, the kit includes instructional materials disclosing means of use of the components included in the kit. The instructional materials may be written, in an electronic form (such as a computer diskette or compact disk) or may be visual (such as video files). The kit may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kit may additionally include buffers and other reagents routinely used for the practice of a particular method. Such kits and appropriate contents are well known to those of skill in the art.

A "label" or "reporter molecule" is chemical or biochemical moiety useful for labeling a nucleic acid or protein entity, e.g., amino acid or antibody. Examples include fluorescent agents, chemiluminescent agents, chromogenic agents, quenching agents, radioisotopes, enzymes, substrates, cofactors, inhibitors, magnetic particles, and other moieties known in the art. Labels or reporter molecules are capable of generating a measurable signal and may be covalently or noncovalently joined to a nucleic acid or protein.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. For example, "contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

The terms "determining," "measuring," "assessing," and "assaying" are used interchangeably and include both quantitative and qualitative measurement, and include determining if a characteristic, trait, or feature is present or not. Assessing may be relative or absolute. Assessing the presence of a target includes determining the amount of the target present, as well as determining whether it is present or absent.

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

An "antigen" refers to a substance that elicits an immunological reaction or binds to the products of that reaction. The term "epitope" refers to the region of an antigen to which an antibody or T cell binds.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding and/or variable region of the intact antibody and/or the Fc region of an antibody which retains FcR binding capability. Examples of antibody fragments include linear antibodies; single-chain antibody molecules; and multispecific antibodies formed from antibody fragments. Preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256, 495-497 (1975), which is incorporated herein by reference, or may be made by recombinant DNA methods (see, e.g., U.S. Pat. No. 4,816,567, which is incorporated herein by reference). The monoclonal antibodies may also be isolated from phage antibody libraries using the techniques described in Clackson et al., Nature, 352, 624-628 (1991) and Marks et al., J Mol Biol, 222, 581-597 (1991), for example, each of which is incorporated herein by reference.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., Proc Natl Acad Sci USA, 81, 6851-6855 (1984); Neuberger et al., Nature, 312, 604-608 (1984); Takeda et al., Nature, 314, 452-454 (1985); International Patent Application No. PCT/GB85/00392, each of which is incorporated herein by reference).

EXAMPLES

Example 1

Generation and Characterization of an Antibody Specific for N-phenylacetamidyl Cys The present invention provided an isolated antibody useful for in situ imaging of S-nitrosylated proteins in cells with high specificity and accuracy.

As illustrated in FIG. 1, precise detection of S-nitrosylated proteins not only requires an antibody specifically targeting the fraction of ascorbate-reduced Cys residues, but also depends on successful and complete blocking of free thiols. For this, it was demonstrated herein that complete blocking of free thiols in cellular proteins can be achieved by the use of two alkylating reagents with hydrophilic (IAM, FIG. 4) and hydrophobic (APIAM, FIG. 5) characteristics sequentially. On the basis of these designs, the inventors established a workflow that constructs two-step blocking and subsequent PAC modification at the time of ascorbate-induced reduction of nitroso-Cys, therefore termed the PAC-switch method, for detection of S-nitrosylated proteins (FIG. 6).

A synthetic alkylating reagent 2-iodo-phenylacetamide (iodoacetanilide, IAN; compound 1 in FIG. 1c) was selected to introduce a high level of phenylacetamidylation on all 35 Cys residues of the recombinant bovine serum albumin (BSA), which had been processed to ensure that it was in its reduced and denatured state (FIG. 1b). The treated BSA was subsequently used for immunization of guinea pig and generation of a strain of polyclonal antibody, named "anti-N-phenylacetamidyl Cys (PAC) antibody".

After affinity purification from serum, the specificity of anti-PAC antibody was tested. Aliquots of total lysates from COS-7 cells that do not express a detectable level of endogenous eNOS (Iwakiri (2006) PNAS, 103: 19777-19782) were incubated with a group of synthetic reagents. These included IAN, iodoacetamide (IAM, compound 2 in FIG. 1c), N-(4-acetylphenyl)-2-iodoacetamide (APIAM, compound 3 in FIG. 1c) and N-(2,3-dimethylphenyl)-2-iodoacetamide (DPIAM, compound 4 in FIG. 1c), which share a common chemical character of Cys alkylation but are structurally diverse. The lysates were subjected to SDS-PAGE, followed by immunoblotting analysis with anti-PAC antibody. As shown in FIG. 1d, the antibody only recognized IAN-treated cellular proteins, but not untreated or other alkylating reagents-reacted lysates. Moreover, the analysis of mixtures from IAN- and IAM-treated samples showed a dose-dependent increase of PAC signal proportional to the level of IAN-reacted lysates (FIG. 1e), suggesting that this antibody targeted phenylacetamidyl Cys in total lysates specifically even in the abundant presence of acetamidyl Cys. The performance of anti-PAC antibodies to recognize cellular proteins with phenylacetamidyl Cys modifications was next tested by immunofluorescence staining. For this, permeabilized COS-7 cells were exposed to IAM, IAN, APIAM or DPIAM and subsequently reacted with anti-PAC antibody for visualization of Cys alkylation. As expected, IAN-treated cells were strongly stained with anti-PAC antibodies, whereas cells exposed to IAM or APIAM were resistant to the binding of antibodies (FIG. 1f). It was noticed that, to a small degree of cross-reaction, anti-PAC antibody recognized DPIAM-treated cells in this analytic format (FIG. 1f). Thus, the use of DPIAM was avoided in the follow-up experiments.

As illustrated in FIG. 1a, the proteins recognized by the antibody would be those originally protected from post-fixing blocking (B) by a stimulus-dependent modification at the susceptible Cys, which was reversed by ascorbate and then being tagged by alkylation (A), consistent with S-nitrosylation of the Cys. The antibody specifically targeted the alkylated Cys after ascorbate-mediated reduction but did not react with the fraction of Cys residues being blocked or any endogenous biomolecules present in cells.

Example 2

Development of the PAC-switch Method for Visualization of Cellular Proteins Susceptible to S-nitrosylation As illustrated in FIG. 1a, precise detection of S-nitrosylated proteins not only requires an antibody specifically targeting the fraction of ascorbate-reduced Cys residues, but also depends on successful and complete blocking of free thiols. Both criteria must be satisfied to avoid false-positive results and to ensure that the information regarding S-nitrosylated proteins being identified is reliable. Having demonstrated the specificity of anti-PAC antibody (FIG. 1), which was reserved for reaction with ascorbate-reduced Cys residues, the inventors next developed a strategy for sufficiently blocking free thiols present in cellular proteins. For this, IAM and APIAM were selected for further tests because their alkylated products did not cross-react with anti-PAC antibody (FIG. 1f. Permeabilized COS-7 cells pre-exposed to IAM or APIAM individually were subsequently incubated with IAN, followed by immunofluorescence staining with anti-PAC antibody. As shown in FIG. 2a, exposure of cells to either reagent markedly decreased, but did not eliminate, the signal detected by anti-PAC antibody. These results indicated that a small fraction of Cys residues in cellular proteins remained in the free thiol form after the reaction with IAM or APIAM, and were thereby susceptible to IAN-mediated phenylacetamidylation. Obviously, the blocking condition was not ideal under such circumstances. To alleviate the influence of free thiols as much as possible, sequential treatment of cells with IAM and APIAM was performed before the final addition of IAN. This procedure ablated the PAC signal in cytosol (FIG. 2a), suggesting that complete blocking of free thiols in cellular proteins requires the use of two alkylating reagents with hydrophilic (IAM) and hydrophobic (APIAM) characteristics sequentially. Based on the results of these tests, a workflow involving two-step blocking and subsequent PAC modification at the time that ascorbate induced a reduction of nitroso-Cys was established. This set of procedures was termed the PAC-switch method, a method that can be used in the detection of S-nitrosylated proteins (FIG. 2b).

To validate the strategy of the PAC-switch method, aliquots of total lysates were collected from untreated and NO donor S-nitroso-N-acetylpenicillamine (SNAP)-treated COS-7 cells, processed following the protocol shown in FIG. 2b, and then subjected to immunoblotting with anti-PAC antibody. Importantly, in the absence of SNAP, the PAC signal was barely detected in total lysates (FIG. 2c, upper panel), indicating successful blocking of cellular proteins by the two-step alkylating reaction. On the other hand, the treatment of SNAP led to significant increases of the PAC signal in a broad range of cellular proteins (FIG. 2c, upper panel). These results suggested that stimulus-induced S-nitrosylation of endogenous proteins can be detected reliably by this method. The effect of N-ethylmaleimide (NEM) for blocking of free thiols was tested in the context of SNAP-induced S-nitrosylation of cellular proteins. As shown in FIG. 2c (upper panel), NEM was unable to eliminate the PAC signal derived from untreated cells. Even though the stimulation of cells with SNAP led to a small increase in PAC signals (FIG. 2c, upper panel), incomplete blocking of free thiols by NEM rendered visualization of S-nitrosylated proteins questionable under the circumstance.

Having demonstrated the drawback of using single alkylating reagent to identify S-nitrosylated proteins, the inventors then examined the potential problem revealed by the widely used biotin switch method, which is entirely dependent upon NEM-mediated blocking of free thiols (Jeffery (2001) Nat Cell Biol, 3: 193-197). As shown in FIG. 2c (lower panel), following the published protocol to process total lysates, the inventors were unable to differentiate the biotin signals of control and the SNAP-treated COS-7 cells, suggesting that a large fraction of biotin-tagged proteins would be false-positive rather than actually being S-nitrosylated. On the other hand, when sequential addition of IAM and APIAM instead of NEM alone was used as the blocking procedure, a significant reduction of biotin signal was observed in untreated sample (FIG. 2c, lower panel). Under this condition, SNAP-promoted S-nitrosylation of cellular proteins was readily detected (FIG. 2c, lower panel). Together, these results showed that it was necessary to use two steps to block free thiols, regardless of whether the PAC switch method or the biotin switch method was used, to identify S-nitrosylated proteins.

The PAC switch method was then used in the format of immunofluorescence staining to visualize S-nitrosylated proteins in COS-7 cells exposed to SNAP. As shown in FIG. 2d, in the presence of ascorbate, which reduced S-nitrosylated Cys readily for IAN-mediated phenylacetamidylation, a robust signal registered by anti-PAC antibody throughout the entire cell was detected. This result indicated that proteins located at various subcellular compartments might be susceptible to S-nitrosylation as long as bioavailable NO is nearby. In an exploration of this possibility, cells stained with anti-PAC antibody were co-stained with specific markers for subcellular organelles. In response to SNAP treatment, fractions of proteins associated with endoplasmic reticulum (ER), Golgi and plasma membrane were likely S-nitrosylated.

Next assays were carried out to examine d whether PTP1B could be S-nitrosylated in cells exposed to NO donor. Both the full-length form and the 37 kDa C-terminally truncated form of GFP-tagged PTP1B were positively stained with anti-PAC antibody, suggesting that ectopically expressed PTP1B in either ER-anchored form or diffused form was susceptible to S-nitrosylation. The same approach was applied to detect S-nitrosylation of endogenous PTP1B. For this, parental COS-7 cells stimulated with SNAP were processed by the PAC switch method and subsequently stained with anti-PAC and anti-PTP1B antibodies. As shown in FIG. 2e, a fraction of paranucleus-localized PTP1B was overlaid with PAC signal in the presence of ascorbate, suggesting that the formation of S-nitrosylated PTP1B in cells exposed to SNAP could be captured by this in situ imaging approach. Together, these findings demonstrated the feasibility of using our newly developed PAC switch method to examine whether and where endogenous PTP1B is S-nitrosylated in endothelium response to insulin stimulation.

Example 3

Figure 3B:
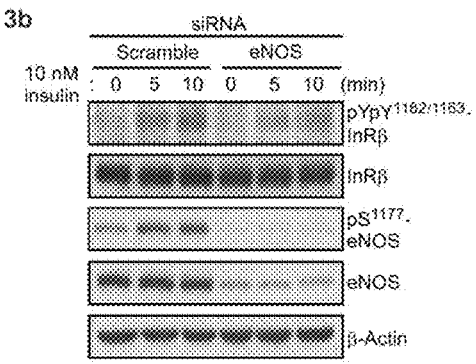
Figure 3C:
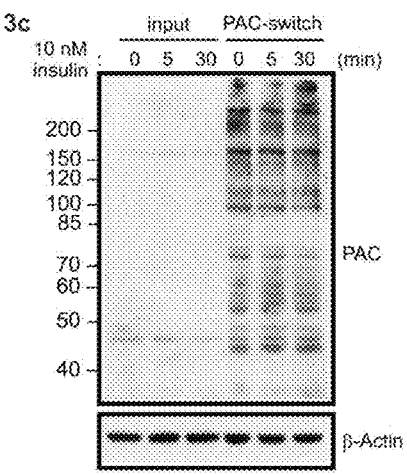
Figure 3D:
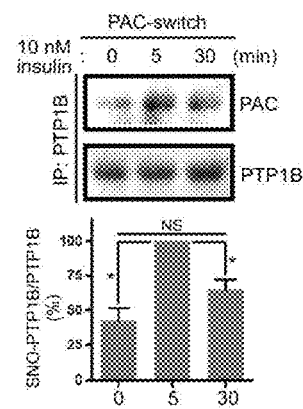

Endogenous PTP1B was Susceptible to S-nitrosylation in Endothelium Stimulated with Insulin In this example, additional assays were carried out to examine whether eNOS-produced NO in endothelium exposed to insulin could enhance insulin responsiveness through S-nitrosylation and hence catalytic inactivation of PTP1B. Signaling events in capillary-derived MS-1 endothelium under insulin stimulation at a physiological concentration (10 nM) was examined. As shown in FIG. 3a, after 2 min of insulin treatment, endothelial NO synthase (eNOS) was activated, concomitant with an initial increase of phosphorylation on the tandem tyrosine motif (Y1162/Y1163) at the activation loop of IR. It was observed that the Y1162/Y1163 motif was robustly phosphorylated at 5 min, peaked at 10 min and significantly dephosphorylated 30 min after insulin stimulation (FIG. 3a). Importantly, insulin-induced phosphorylation of the Y1162/Y1163 motif was NO-dependent and this signaling event of IR was significantly diminished in eNOS-ablated MS-1 cells (FIG. 3b). Based on these observations, it was hypothesized that activation of IR within the first 5 min might require NO-dependent S-nitrosylation and inactivation of PTP1B, thus allowing IR, which is a bona fide substrate of PTP1B (Salmeen et al., *Mol Cell* 6, 1401-12 (2000)), to be fully activated. To test this hypothesis, MS-1 cells exposed to insulin for 5 min or 30 min were harvested and total lysates were subsequently processed following the PAC switch method. Aliquots of total lysates and immunoprecipitated PTP1B were then subjected to immunoblotting with anti-PAC antibody. The above results demonstrated that, although PAC signals in total lysates were indistinguishable between control and treated samples (FIG. 3c), stimulation of cells with insulin for 5 min induced an increased level of PTP1B S-nitrosylation (FIG. 3d). Interestingly, the inducible S-nitrosylation of PTP1B was transient as its level was markedly reduced after 30 min of insulin stimulation (FIG. 3d).

Example 4

In Situ Imaging of Insulin-induced PTP1B S-nitrosylation in Endothelium

Figure 4A:
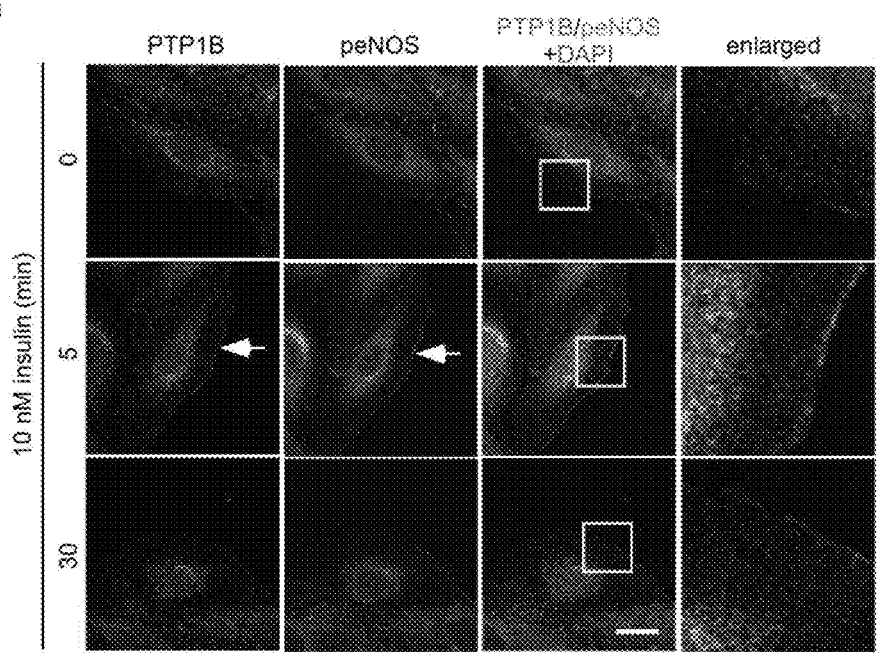
FIG. 4a and FIG. 4b: Co-localization of endogenous PTP1B and S-nitrosylated proteins to endothelial cell periphery in response to insulin stimulation.
Figure 4B:
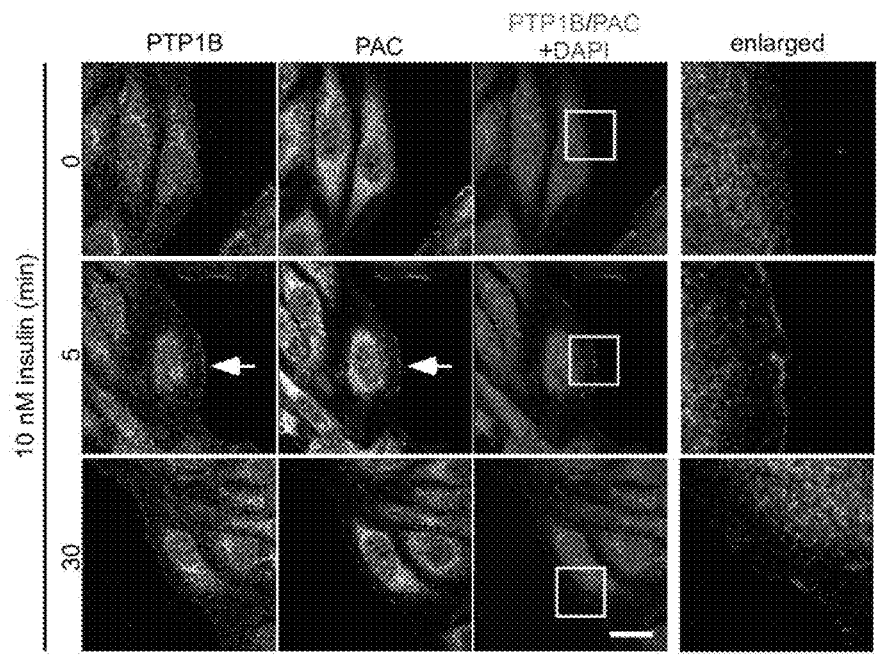
Figure 5A:
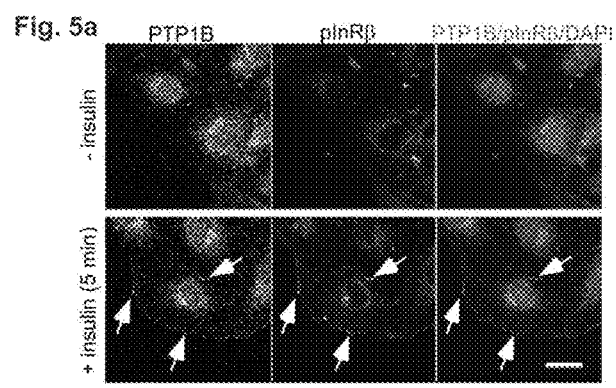
FIG. 5a, FIG. 5b, and FIG. 5c: Co-localization of S-nitrosylated PTP1B and activated insulin receptor to endothelial cell periphery in response to insulin stimulation.

The subcellular localization of S-nitrosylated PTP1B in endothelium response to insulin stimulation was examined. Since eNOS-induced NO production promotes protein S-nitrosylation, the inventors began by testing whether endogenous PTP1B was co-localized with phosphorylated and hence activated eNOS in cells exposed to insulin. As shown in FIG. 4a, after 5 min of insulin stimulation, a fraction of PTP1B concentrated at the cell periphery was co-stained with $Ser^{1177}$-phosphorylated form of eNOS. Co-localization between PTP1B and phosphorylated eNOS decreased dramatically 30 min after stimulation (FIG. 4a). These results suggested that eNOS-produced NO might direct transient S-nitrosylation of PTP1B, which was translocated to cell periphery during endothelial insulin signaling. To test this hypothesis, untreated cells and cells exposed to insulin for 5 min or 30 min were fixed and subsequently processed by the PAC switch method. In addition to being stained with anti-PAC antibody, cells were also stained with anti-PTP1B antibodies. As shown in FIG. 4b, PTP1B was mostly ER-localized without obvious overlapping of PAC signals in untreated cells, consistent with its low level of S-nitrosylation depicted by immunoblotting analysis under the same condition (FIG. 3d). In contrast, a pool of PTP1B translocated to the cell periphery showed clear co-staining with anti-PAC antibody in response to insulin stimulation for 5 min (FIG. 4b), concomitant with a robust level of PTP1B S-nitrosylation (FIG. 3d). The association between PAC and PTP1B signals was significantly diminished at the cell border after 30 min of insulin stimulation (FIG. 4b). Clearly, these results showed that initial S-nitrosylation of PTP1B localized to the cell periphery was transient and reversible. It was proposed that the reduction of S-nitrosylated PTP1B 30 min after insulin treatment (FIGS. 3d and 4b) allowed this pool of PTP1B to regain activity, leading to dephosphorylation of IR (FIG. 3a).

Example 5

Figure 5B:
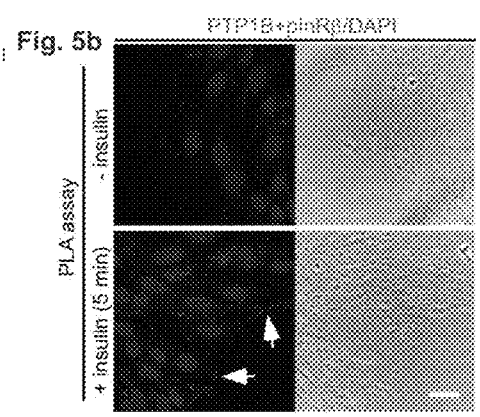

Association Between S-nitrosylated PTP1B and Activated IR at the Cell Periphery in Endothelium Exposed to Insulin The localization of S-nitrosylated PTP1B to the cell periphery shortly after insulin stimulation (FIG. 4b) led to investigation to find out whether this pool of PTP1B might be already recruited by the activated form of endothelial IR. For this, the complex formation between endogenous PTP1B and activated IR was examined in insulin-treated endothelium. MS-1 cells exposed to insulin for 5 min were stained with anti-PTP1B and anti-pYpY$^{1162/1163}$-IR antibodies. Results in FIG. 5a clearly showed the colocalization of PTP1B and pYpY$^{1162/1163}$-IR (pIR) at the cell periphery, suggesting that the association between the two in the plasma membrane vicinity occurred in an insulin stimulation-dependent manner. This possibility was explored using the imaging approach of the proximity ligation assay (PLA), which generates signals only if neighboring proteins are within 40 nm (Yamazaki et al., Genes Cells 14, 425-34 (2009), Bobrich et al. Int J Obes (Lond) 35, 1385-94 (2011), and Salmon et al., Circ Res 111, 685-96 (2012)). As expected, control cells without insulin treatment did not show PLA signal at the cell periphery (FIG. 5b). In contrast, a cluster of PLA signals was detected along the cell boundary and at the borderline between two cells in response to insulin stimulation for 5 min (FIG. 5b), indicating that ligand-activated IR was soon complexed with PTP1B.

Figure 5C:
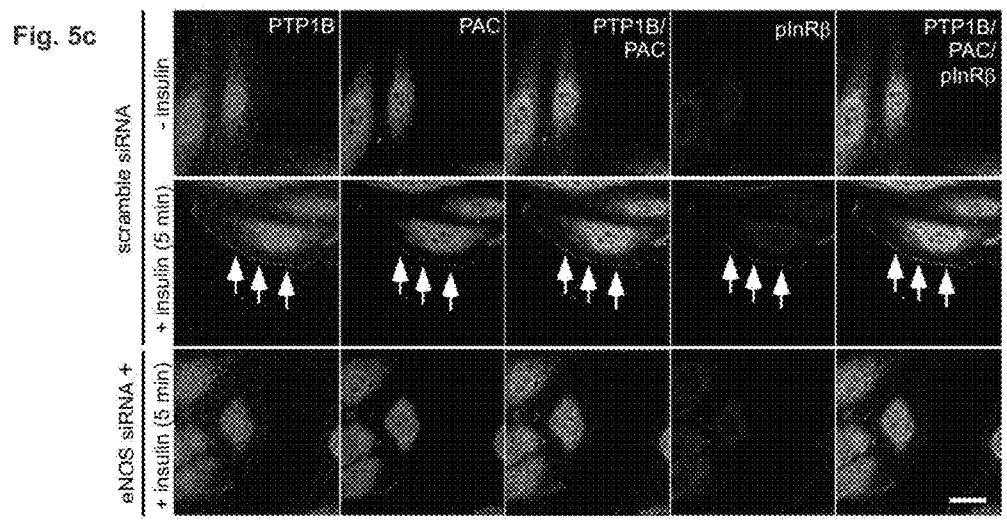

It was then examined whether PTP1B associated with pIR at the cell periphery was the pool of PTP1B undergoing S-nitrosylation. For this, MS-1 cells exposed to insulin for 5 min were processed by the PAC switch method, followed by immunofluorescence detection to visualize S-nitrosylated PTP1B and pIR. In insulin-stimulated control cells where endogenous eNOS was Ser$^{1177}$-phosphorylated (FIG. 4a), PTP1B which was translocated to the cell periphery was co-stained with anti-PAC and anti-pYpY$^{1162/1163}$-IR antibodies (FIG. 5c), suggesting that the complex formation between S-nitrosylated PTP1B and activated IR occurred in a ligand-dependent manner. Importantly, co-localization of PTP1B, PAC and pIR at the cell border was abrogated when eNOS was ablated by specific siRNA (FIG. 5c). Taken together, these data indicated that only in the presence of eNOS-produced NO, PTP1B in the S-nitrosylated form was associated stably with plasma membrane-localized pIR.

Example 6

Figure 6A:
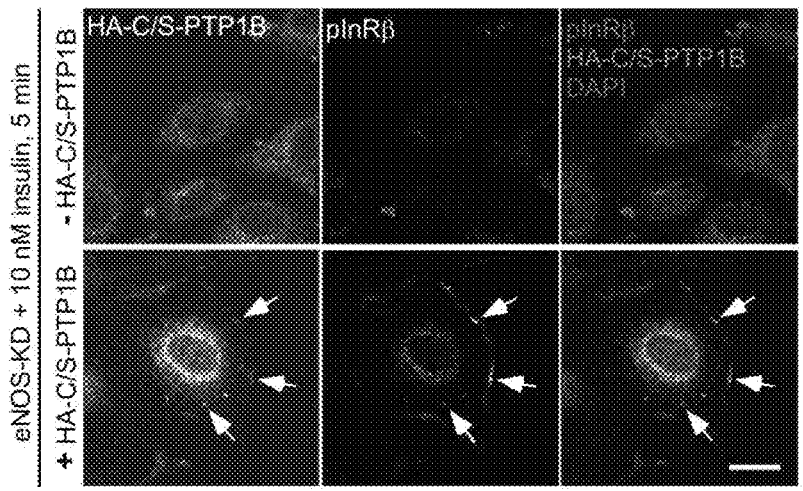
FIG. 6a and FIG. 6b: Restoration of insulin responsiveness in eNOS-ablated endothelium by ectopic expression of C215S mutant form of PTP1B.
Figure 6B:
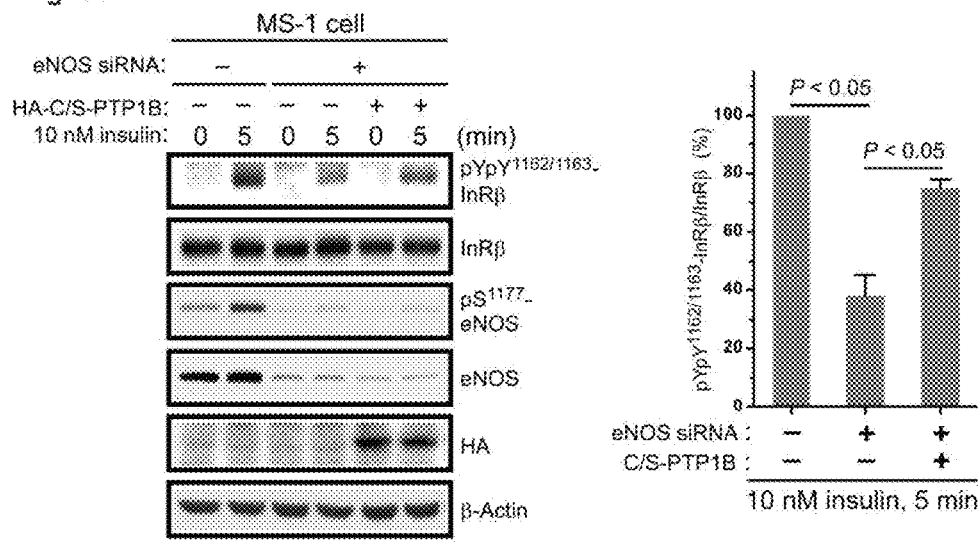

NO-promoted Insulin Responsiveness in Endothelium Depends on PTP1B S-nitrosylation of the Active-site Cys Having demonstrated ligand-dependent co-localization of S-nitrosylated PTP1B and activated IR (FIG. 5), the inventors proposed that the formation of nitrosothiol on the active-site Cys215 of PTP1B in this particular pool of IR complex might be the primary effect of NO's enhancement of endothelial insulin signaling. To test this hypothesis, the C215S mutant form of PTP1B (PTP1B-C215S), which mimics the active-site Cys215 S-nitrosylated, hence the inactivated form of PTP1B, was ectopically expressed in eNOS-ablated MS-1 cells. This PTP1B-C215S might function as a dominant negative mutant to compete with endogenous PTP1B, which would be in the reduced and active form during eNOS knockdown, for the IR complex formation. In attempting to understand the role of PTP1B-C215S in regulating insulin responsiveness without the influence of intrinsic NO, attention was drawn to the subcellular localization of activated IR in eNOS knockdown MS-1 cells exposed to insulin for 5 min. As expected, without PTP1B-C215S, IR in its pYpY$^{1162/1163}$ form was barely detected in eNOS-ablated cells (FIG. 6a). In contrast, even in the absence of endogenous eNOS, ectopic expression of PTP1B-C215S promoted the accumulation of activated IR at the cell periphery (FIG. 6a). Interestingly, this fraction of activated IR was co-stained with PTP1B-C215S in eNOS knockdown cells (FIG. 6a), suggesting that insulin-induced association of catalytically inactive PTP1B with pIR was independent of NO production. The degrees of insulin signaling were then monitored by IR pYpY$^{1162/1163}$ phosphorylation in eNOS-ablated cells with either mock transfection or ectopic expression of PTP1B-C215S. As expected, in response to eNOS knockdown, endothelial insulin responsiveness was significantly decreased (FIG. 6b), presumably due to lack of NO effect on reversible inactivation of PTP1B. Importantly, such eNOS ablation-caused defect of insulin signaling was significantly restored by ectopic expression of PTP1B-C215S (FIG. 6b). Collectively, these results indicates that NO plays a critical role in active-site Cys215 S-nitrosylation of PTP1B soon after insulin stimulation. This NO-dependent modification inhibits PTP1B in the complex of pIR, thus allowing downstream signaling to propagate for promotion of endothelial insulin responsiveness.

Example 7

Targeted Mass Spectrometric Determination of IAN-tagged Catalytic Cys463 of Endogenous SHP-2 Isolated from Insulin-treated Cells In this example, the above-described PAC-switch method was used on another tyrosine phosphatase SHP-2. Briefly, two samples, "IAN control," and "Insulin-treated," were analyzed using mass spec analysis. For the IAN control, an aliquot of MS-1 cell lysates was exposed to IAN in vitro. For the insulin-treated sample, MS-1 cells were exposed to insulin (10 nM) for 5 minutes, the cells then lyzed, and an aliquot of lysates was processed by the PAC-switch method. Endogenous SHP-2 protein was immunoprecipitated, followed by trypsin digestion for the subsequent analysis by the Q Exactive HF operated in a parallel-reaction monitoring mode. Two proteotypic peptides of SHP-2 as well as IAM- and IAN-labeled catalytic Cys (C463) containing peptides were selected as targets.

Figure 7:
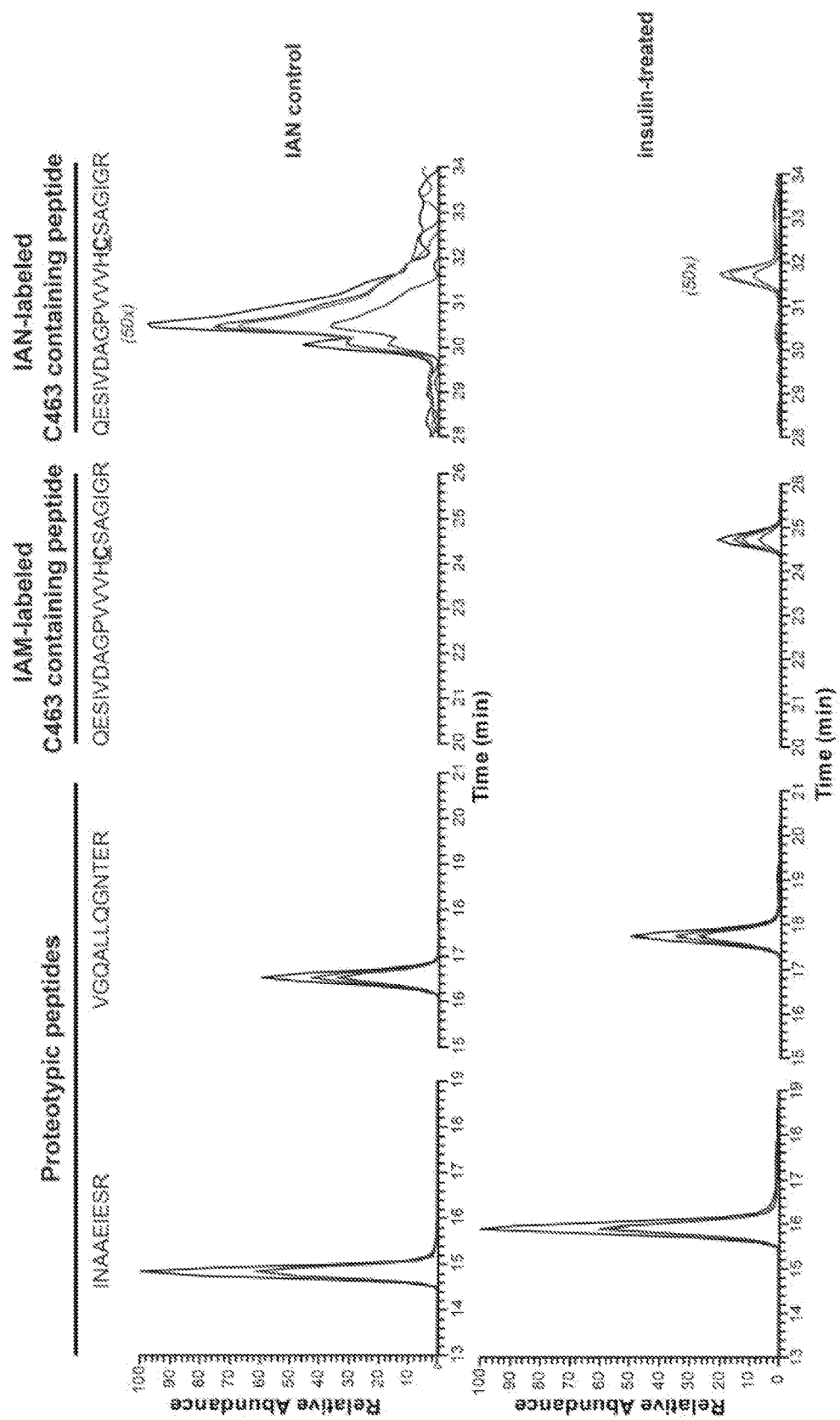
FIG. 7 is diagrams showing targeted mass spectrometric determination of IAN-tagged catalytic Cys463 of endogenous SHP-2 isolated from insulin-treated cells, where extract ion currents of four most abundant fragment ions (SEQ ID No: 3-6) of the individual targets were color-coded and overlapped.

As shown in FIG. 7, extract ion currents of four most abundant fragment ions of the individual targets were color-coded and overlapped. It was found that that the intensities of transitions from the IAN-labeled C463-containing peptide were magnified by 50 folds. All targeted transitions are (SEQ ID Nos: 3-6) listed in the table below.

| Peptide sequence | m/z | charge | transitions |
|---|---|---|---|
| Proteotypic peptides | | | |
| INAAEIESR | 501.76 | 2 | y7 (775.40) |
| | | | y6 (704.36 |
| | | | y5 (633.32) |
| | | | y8 (889.44) |
| VGQALLQGNTER | 643.35 | 2 | y7 (817.42) |
| | | | y6 (704.33) |
| | | | y5 (576.27) |
| | | | y8 (930.50) |
| IAM-labeled C463 | | | |
| QESIVDAGPVVVHCSAGIGR | 684.35 | 3 | y8 (857.40) |
| | | | y9 (956.47) |
| | | | y7 (720.34) |
| | | | y10 (1055.54) |
| IAN-labeled C463 | | | |
| QESIVDAGPVVVHCSAGIGR | 709.69 | 3 | y8 (933.45) |
| | | | y9 (1032.50) |
| | | | y7 (796.38) |
| | | | y10 (1131.57) |

The results shown in this analysis clearly demonstrate that the originally S-nitrosylated Cys463 on SHP-2 in insulin-treated MS-1 cells was switched to the IAN-targeted modification, thus being identified by mass spectrometry. This further demonstrates the reliability of the methodology disclosed in this application.

Discussion

In the present disclosure, it is shown for the first time that endogenous PTP1B was targeted directly by intrinsic NO in endothelium soon after stimulation with insulin. NO-induced S-nitrosylation preferentially occurred on the active-site Cys215 of PTP1B (Chen et al. *J Biol Chem* 283, 35265-72 (2008).), suggesting that NO plays a critical role in promoting endothelial insulin signaling through S-nitrosylation-dependent inactivation of PTP1B, a phosphatase long known to antagonize IR activity (Salmeen et al., *Mol Cell* 6, 1401-12 (2000), Elchebly et al. *Science* 283, 1544-8 (1999); Klaman et al. *Mol Cell Biol* 20, 5479-89 (2000). This hypothesis was supported in this study by the observed effect of the ectopically expressed phosphatase-inactive C215S mutant form of PTP1B on restoration of insulin signaling, which was otherwise alleviated in endothelium where endogenous eNOS was ablated by RNAi.

The findings disclosed herein show a newly discovered function of NO in which it specifically inactivates PTP1B for the promotion of endothelial insulin responsiveness (FIG. 7). Previous studies have suggested that eNOS-mediated NO production is essential for physiological homeostasis of insulin signaling (Shankar (2000) Diabetes 49: 684-687; Duplain (2001) Circulation, 104: 342-345; Cook (2004) Diabetes 53: 2067-2072) and insulin-dependent glucose uptake of skeletal muscle (Baron (1995), Am J Physiol, 269: E709-715; Roy (1998) Am J Physiol, 274: E692-699; Kubota et al Cell Metabolism 2011). Nevertheless, the mechanism underlying such NO-promoted insulin responsiveness in endothelium remained elusive. With the new evidence provided by this current study, it is now clear that the activity of PTP1B is temporarily inhibited by NO over the duration of signaling enhancement directed by ligand-bound IR. The finding described herein thus illustrates how endothelial insulin responsiveness can be boosted for the effective delivery of insulin to skeletal muscle.

It was shown that insulin induces rapid association between PTP1B and phosphorylated eNOS near cell boundary (FIG. 4a), and that this pool of translocalized PTP1B is S-nitrosylated (FIG. 4b). Based on these observations, one might predict that PTP1B located at the cell periphery would be NO-targeted due to the presence of adjacent pSer$^{1177}$-eNOS, which has been considered as the activated and NO-produced form of eNOS in insulin-stimulated endothelium (Montagnani et al (2001) JBC, 276: 30392; Montagnani et al (2002) Mol Endo, 16: 1931). If this were the case, the pool of PTP1B might remain in its reduced form while being translocated to the cell periphery before gaining access of NO generated by insulin-activated eNOS nearby. However, the findings of one recent work suggested an alternative model. That study demonstrated that endogenous eNOS is mostly localized to the perinuclear region in endothelium under the ground state (Wang et al (2009) Mol Endo, 23: 1613). Interestingly, insulin stimulation induced NO production rapidly and transiently before eNOS together with caveolin-1 were translocated to plasma membrane (Wang et al (2009) Mol Endo, 23: 1613). Data from the same study further suggested that the trafficking of eNOS to the cell periphery causes inhibition of its activity despite a persistent Ser$^{1177}$ phosphorylation (Wang et al (2009) Mol Endo, 23: 1613), leading to a decline of NO production in endothelium shortly after exposure to insulin. Considering the results of those previous experiments in conjunction with our current observations (FIG. 4), the inventors proposed that endogenous PTP1B, which is anchored on the ER membrane and concentrated in close vicinity to paranucleus-localized eNOS under the ground state, would be targeted by NO on site immediately after insulin stimulation. The process of S-nitrosylation might continue for the duration of insulin-mediated translocation of PTP1B and eNOS to the cell periphery. It is likely that once they reach to the destination at the cell boundary, the pool of PTP1B is fully S-nitrosylated and inactivated (FIG. 5), whereas pSer$^{1177}$-eNOS is now in the complex with caveolin-1 thus being catalytically inactive.

The finding that activated IR and S-nitrosylated PTP1B colocalized during the initial phase of insulin responsiveness in endothelium (FIG. 5) is interesting and important. With this discovery, the inventors are able to explain clearly how to prevent the rapid "switch-off" of insulin signaling from immediate association between PTP1B and IR in cells under such stimulation. It was observed a decade ago that PTP1B interacts with IR in a diverse array of insulin responsive cells soon after exposed to insulin. The effect of insulin on the dynamic interaction of the IR with a trapping mutant form of PTP1B was documented as early as 30 seconds in living human embryonic kidney cells (Boute et al (2003) EMBO Rep, 4: 313-319), suggesting that the tyrosine kinase activity of IR may drive the recruitment of PTP1B in this context. It was subsequently shown that the association between an inactive mutant form of PTP1B and IR peaked at 5 min in adipocytes stimulated with insulin, and that their interaction was independent of IR internalization (Shi et al (2004) J Biochem 136: 89-96). Moreover, in vivo imaging using Bimolecular Fluorescence Complementation (BiFC) in another study demonstrated that not only a trapping mutant or catalytically inactivate mutant form but also a WT form of PTP1B could target IR at the plasma membrane of human embryonic kidney cells within 5-10 min post insulin stimulation (Anderie et al (2007) Cell Signaling, 19:582-592). Together with new evidence provided by this current study (FIGS. 5a and 5b), it is now understood d that a pool of endogenous PTP1B can interact with activated pIR at the cell border of endothelium soon after exposure to insulin. Importantly, it was further demonstrated herein that S-nitrosylation is an essential mechanism preventing the immediate dephosphorylation of IR by PTP1B already present in the same complex (FIG. 5c). As discussed above, since this pool of PTP1B is likely targeted by NO while traveling from the paranuclear region to the cell border, PTP1B may be in its S-nitrosylated and catalytically inactive form upon docking at its destination, the activated IR complex. This would explain why endothelial insulin responsiveness could be further enhanced for an extended period even after PTP1B was already associated with pIR (FIG. 3a).

It is shown above that endogenous PTP1B, which is anchored to the cytosolic surface of the ER membrane, can interact with phosphorylated IR at the cell border in endothelium exposed to insulin (FIG. 5). Obviously, dynamic extension of the ER membrane plays a key role in targeting PTP1B to the plasma membrane region upon insulin stimulation. Recent studies have demonstrated that ER membranes are positioned close to the plasma membrane by microtubules (Monteleone (2012) Plos One 7: e38948). This finding suggests that dynamic ER membrane network might carry PTP1B to its regulatory pTyr site of substrates located at the plasma membrane, such as examples shown previously (Haj (2012) Plos One 7: e36633) and also in the present work. However, this mechanism may only provide the opportunity of random contacts between ER membranes and plasma membranes, and may therefore be insufficient to establish the specific interaction of PTP1B with pIR. A recent study revealed an important role of the adaptor protein Nck, which binds to PTP1B constitutively through the N-terminal SH3 domain, in recruiting PTP1B to the activated IR in signaling response to insulin stimulation (Wu (2011) BJ, 439: 151-159). Together with new results presented in the current work, it is proposed that SH2 domains of Nck interact with pTyr residues of IR, leading to the inducible recruitment of Nck/S-nitrosylated PTP1B complex to the specific sites at the plasma membrane where activated IR is located. This pool of S-nitrosylated PTP1B may subsequently undergo Cys reduction, leading to rapid rebound of its phosphatase activity for down-regulating pIR in the same protein complex before dissociation of Nck/PTP1B complex from dephosphorylated IR.

The PAC-switch method allows one to identify the new role of NO in promoting endothelial insulin signaling through S-nitrosylation of PTP1B. With the development of new reagent and methodology in detection of S-nitrosylated proteins in situ, the inventors have demonstrated that transient inactivation of PTP1B controlled by intrinsic NO plays an indispensable role in the process of endothelial insulin responsiveness. These findings open a new avenue for understanding the previously unexplored interplay between reversible cysteine S-nitrosylation and tyrosine phosphorylation that coordinate to regulate insulin delivery across the endothelial barrier.

Methods

Reagents

Freund's incomplete adjuvant, S-nitroso-N-penicillamine (SNAP), L-cysteine, ascorbate, N-(4-acetylphenyl)-2-iodo-acetamide (APIAM), N-(2,3-dimethylphenyl)-2-iodoacetamide (DPIAM), and insulin were purchased from Sigma. Iodoacetamide (IAM) was from GE Healthcare, and 2-iodo-N-phenylacetamide (iodoacetanilide, IAN) was from Cambridge Isotope Laboratories. Tris(2-carboxyethyl)phosphine (TCEP) was from Thermo Fisher Scientific. The 21-nucleotide siRNA duplexes against mouse eNOS were purchased from Dharmacon Thermo Scientific. Two oligonucleotides, 5'-GAUCCUAACUUGCCCUGCAUU-3' (J-040956-07, SEQ ID No: 1) and 5'-GAAUGGAAGUGGUUCAGC-UUU-3' (J-040956-08, SEQ ID No: 2), were chosen for knockdown of eNOS. Purified recombinant human PTP1B (C-terminally truncated 37 kDa) was described previously (Chen et al. *J Biol Chem* 283, 35265-72 (2008)). The cDNA construct of EGFP-tagged full-length PTP1B was established in a previous study (Haj et al. *PLoS One* 7, e36633 (2012)), and was used as a template to generate the EGFP-tagged C-terminally truncated human PTP1B. The HA-tagged C215S (C/S) mutant form of full-length PTP1B was constructed by site-direct mutagenesis using the WT form of human PTP1B as the template and then subcloned into pcDNA3.1 vector. The following antibodies were purchased from various vendors: GAPDH, insulin receptor beta-chain (InRβ), PTP1B for immunoprecipitation (sc-1718-R) and for immunoblotting (sc-1718-G) from Santa Cruz; PTP1B (clone 15 for immunofluorescence staining) from BD; tubulin from Sigma; phospho-specific pYpY$^{1162/1163}$-InRβ from Invitrogen; eNOS and phospho-specific pS$^{1177}$-eNOS (for immunoblotting) from BD; pS$^{1177}$-eNOS (for immunofluorescence staining) from Cell Signaling; HA from Millipore. Alexa 488-conjugated donkey anti-mouse IgG, Alexa 555-conjugated donkey anti-rabbit IgG, Alexa 555-conjugated goat anti-guinea pig IgG, and ProLong Gold antifade reagent were purchased from Invitrogen. Protein A magnetic Sepharose Xtra, protein A-Sepharose, and protein G-Sepharose beads were from GE Healthcare.

Cell Culture and Transient Transfection

Monkey kidney epithelial COS-7 cells were routinely maintained in high glucose Dulbecoo's modified Eagle's medium (DMEM) supplemented with 10% fetal bovine serum (FBS). Mouse endothelial MS-1 cells derived from capillary were maintained in high glucose DMEM supplemented with 5% FBS. For knockdown of endogenous eNOS and ectopic expression of HA-tagged C/S-PTP1B, MS-1 cells were mixed with siRNA (150 pmol with 7×10$^5$ cells) and plasmid DNA (1.5 μg with 7×10$^5$ cells), then electroporated by the Neon™ Transfection System (Invitrogen) according to the manufacturer's instructions. After electroporation, cells were maintained for additional 42 h followed by serum starvation for 6 h before insulin stimulation.

Production of Anti-phenylacetamidyl Cysteine (Anti-PAC) Antibody

Carrier protein bovine serum albumin (BSA, 3 mg/ml) was treated with 50 mM 1,4-dithioerythritol in buffer containing 20 mM Tris-HCl (pH 8.0), 5 mM EDTA, and 8 M urea at 37° C. for 1 h. An equal volume of 20% trichloroacetic acid was added into the solution with brief mixing. After addition of 10× volume of acetone, the whole solution was vortexed and kept at −20° C. for overnight. Pellet was collected by centrifugation and washed with acetone. The pellet was then dissolved in 1 ml buffer containing 100 mM sodium bicarbonate (pH 9.4), 1% SDS, and 8 M urea. Iodoacetanilide (3 mg/0.1 ml) was prepared in DMSO and then added into the BSA solution followed by incubation at 37° C. for 2 h. After spinning centrifugation-dialysis using Concentrators (Pierce), the BSA protein with its Cys residues already phenylacetamidylated was re-suspended in PBS to form the antigen solution. Before injection, the antigen solution was thoroughly mixed with an equal volume of Freund's incomplete adjuvant. Approximately 200 µg of antigen BSA protein was injected subcutaneously into the back of a guinea pig during each biweekly immunization. Ten days after the fifth injection, the blood was withdrawn by heart puncture, and serum was stored at 4° C.

Validation of Anti-PAC Antibody Performance

For immunofluorescence staining, cells grown on coverslips were fixed with 4% paraformaldehyde in PBS for 15 min and permeabilized with 0.1% Triton X-100 in PBS for 5 min at room temperature. Samples were reacted with 1 mM IAM, APIAM, DPIAM, or IAN respectively in HEN buffer (100 mM HEPES, 1 mM EDTA, 0.1 mM neocuproine, pH 8.0) containing 5 mM TCEP and 10% DMSO (except IAM) at 37° C. for 30 min. For sequential blocking test, the concentrations of compounds were 50 mM IAM, 1 mM APIAM, and 1 mM IAN. All labeling reactions were performed in the dark. After washing, samples were blocked with 5% BSA in PBS for 1 h at room temperature, and then incubated with anti-PAC antibody overnight at 4° C. (5% BSA in PBS). Signals were generated by Alexa 555-conjugated goat anti-guinea pig IgG for 1 h at room temperature. Nucleus was stained by DAPI (0.5 µg/ml) and coverslips were mounted with ProLong Gold antifade reagent. Images were obtained from Olympus BX50 fluorescent microscope. For immunoblotting detection, cells were harvested in lysis buffer containing 20 mM HEPES (pH 7.4), 150 mM NaCl, 1% NP-40, and protease inhibitors. Total lysate proteins (harvested from COS-7 cells) were treated with 2 mM IAM, APIAM, DPIAM, or IAN, respectively. All labeling reactions were performed in the dark for 1 h at 37° C. in the buffer containing 25 mM ammonium bicarbonate (pH 8.0) and 5 mM TCEP. Then, total lysates (10 µg) were subjected to immunoblotting with anti-PAC antibody.

Detection of Protein S-nitrosylation by the PAC-switch Method in Total Lysates

Cells were harvested in lysis buffer containing 25 mM HEPES (pH 7.4), 50 mM NaCl, 100 mM EDTA, 1% NP-40, 0.5 mM PMSF, and protease inhibitors. An aliquot of total lysates (800 µg) was reacted with 50 mM IAM (the first-step blocking of free thiols) in HEN buffer with 2.5% SDS at room temperature for 30 min. Proteins were precipitated by cold acetone (100%) at −20° C. for 20 min and collected by centrifugation at 2000×g for 5 min, then washed with cold acetone (70%) 3 times. The sample was next reacted with 1 mM APIAM (the second-step blocking of free thiols) in HEN buffer containing 2.5% SDS and 10% DMSO at 37° C. for 30 min. After precipitation and washing as described above, samples were incubated with 20 mM ascorbate and 0.5 mM IAN in HEN buffer containing 1% SDS and 10% DMSO at room temperature for 1 h. Proteins were precipitated, washed, and then resuspended in 10× diluted HEN buffer (to make final=1×HEN buffer) with 1% SDS. All steps described above were performed in the dark. Aliquots of total lysate (20 µg) were subjected to immunoblotting, and phenylacetamidylated Cys residues in cellular protein were detected by anti-PAC antibody. To examine S-nitrosylation of endogenous PTP1B, MS-1 cells were lysed and total lysates were processed by the PAC-switch method as described above. After final resuspension, the concentration of SDS in total lysates was diluted by PBS to 0.2%. For immunoprecipitation, anti-PTP1B antibody (sc-1718-R, 8 µg each reaction) was first immobilized on beads in the mixture containing equal amounts of protein A- and G-Sepharose, then added into an aliquot of total lysate (0.6 mg) followed by incubation at 4° C. for overnight. Immunoprecipitated PTP1B was eluted by boiling beads in loading buffer containing 60 mM Tris-HCl (pH 6.5), 2% SDS, 0.05% bromophenol blue, 5% β-mercaptoethanol, and 10% glycerol for 5 min. Equal volumes of protein elutes were subjected to immunoblotting with anti-PAC and PTP1B (sc-1718-G) antibodies.

In Situ Imaging of Protein S-nitrosylation Detected by the PAC-switch Method

Cells grown on coverslips were fixed with 4% paraformaldehyde in PBS for 15 min and then permeabilized with 0.1% Triton X-100 in PBS at room temperature for 5 min. The first-step blocking of free thiols was performed with 50 mM IAM in HEN buffer at room temperature for 30 min. Samples were washed with HEN buffer (5 min, 3 times), and then incubated with 2 mM APIAM in HEN buffer containing 10% DMSO at 37° C. for 30 min for the second-step blocking After washing (HEN buffer plus 10% DMSO, 5 min, 3 times), samples were incubated with 20 mM ascorbate and 0.5 mM IAN in HEN buffer containing 10% DMSO at room temperature for 1 h. All labeling reactions were kept in the dark. After final washes with HEN buffer (10% DMSO), samples were blocked with 5% BSA in PBS at room temperature for 1 h, followed by incubation with anti-PAC antibody or other primary antibodies in 5% BSA (in PBS) at 4° C. for overnight. After washes, samples were incubated with Alexa 555-conjugated goat anti-guinea pig IgG (for anti-PAC antibody to detect phenylacetamidylated Cys residues in cellular proteins) and other fluorochrome-conjugated secondary antibodies at room temperature for 60 min. Nucleus was stained by DAPI (0.5 µg/ml) before coverslips finally mounted with ProLong Gold antifade reagent. Images were obtained from Olympus BX50 fluorescent microscope or Zeiss LSM510 inverted confocal microscope.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

We claim:

1. A method for determining the presence or absence of protein S-nitrosylation or oxidation in a sample, the method comprising:

blocking free thiols in the sample with thiol-reactive alkylating agents selected from the group consisting of iodoacetamide (IAM), N-(4-acetylphenyl)-2-iodoacetamide (APIAM) and N-(2,3-dimethylphenyl)-2-iodoacetamide (DPIAM);

contacting the sample with one or more reducing agents;

reacting with a 2-Iodo-N-phenylacetamide (IAN) to form N-phenylacetamidyl cysteine; and detecting N-phenylacetamidyl cysteine by an anti-N-phenylacetamidyl cysteine (PAC) antibody, thereby determining the presence or absence of protein S-nitrosylation or oxidation.

2. The method of claim 1, wherein the one or more reducing agents comprise ascorbate, $Cu^{2+}$, $Hg^2$, Tris-(2-carboxyethyl) phosphine (TCEP), Tris-(hydroxypropyl) phosphine (THP), Dithiothreitol (DTT), Tris(3-hydroxypropyl)phosphine (THPP), cysteine, glutathione or combinations thereof.

3. The method of claim 1, wherein the antibody (i) specifically binds to a moiety having the structure of formula (A):

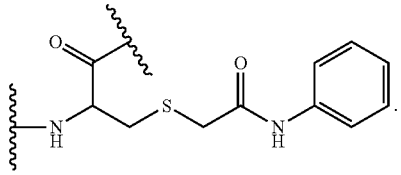

(A)

and (ii) is incapable of binding to a moiety having the structure of formula either (B) or (C):

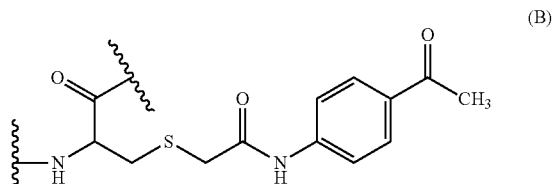

(B)

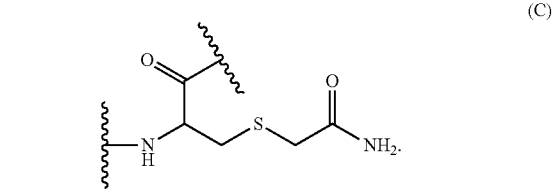

(C)

4. The method of claim 1, wherein the antibody is incapable of binding to a moiety having the structure of formula (D):

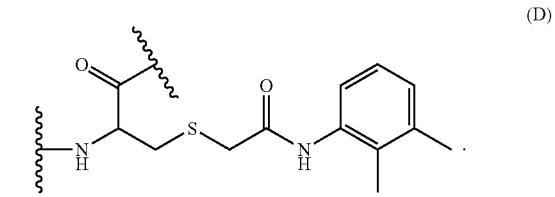 [SMILES: *NC(CSCC(=O)Nc1cccc(C)c1C)C(*)=O ; "."]

(D)

5. The method of claim 1, wherein the antibody is a polyclonal antibody or a monoclonal antibody.

6. The method of claim 1, wherein the method is for determining the presence or absence of protein S-nitrosylation, and the one or more reducing agents comprise ascorbate, $Cu^{2+}$, or $Hg^2$.

7. The method of claim 1, wherein the method is for determining oxidation and the one or more reducing agents comprise Tris-(2-carboxyethyl)phosphine (TCEP), Tris-(hydroxypropyl)phosphine (THP), Dithiothreitol (DTT), Tris(3-hydroxypropyl)phosphine (THPP), cysteine, glutathione or combinations thereof.

* * * * *

SEQUENCE LISTING

<160> NUMBER OF SEQ ID NOS: 6

<210> SEQ ID NO 1
<211> LENGTH: 21

```
<212> TYPE: RNA
<213> ORGANISM: Artificial Sequence
<220> FEATURE:
<223> OTHER INFORMATION: oligo

<400> SEQUENCE: 1
gauccuaacu ugcccugcau u                                              21

<210> SEQ ID NO 2
<211> LENGTH: 21
<212> TYPE: RNA
<213> ORGANISM: Artificial Sequence
<220> FEATURE:
<223> OTHER INFORMATION: oilog

<400> SEQUENCE: 2
gaauggaagu gguucagcuu u                                              21

<210> SEQ ID NO 3
<211> LENGTH: 9
<212> TYPE: PRT
<213> ORGANISM: Artificial Sequence
<220> FEATURE:
<223> OTHER INFORMATION: trypsin digested fragment

<400> SEQUENCE: 3

Ile Asn Ala Ala Glu Ile Glu Ser Arg
1               5

<210> SEQ ID NO 4
<211> LENGTH: 12
<212> TYPE: PRT
<213> ORGANISM: Artificial Sequence
<220> FEATURE:
<223> OTHER INFORMATION: trypsin digested fragment

<400> SEQUENCE: 4

Val Gly Gln Ala Leu Leu Gln Gly Asn Thr Glu Arg
1               5                   10

<210> SEQ ID NO 5
<211> LENGTH: 20
<212> TYPE: PRT
<213> ORGANISM: Artificial Sequence
<220> FEATURE:
<223> OTHER INFORMATION: IAM-labeled C463

<400> SEQUENCE: 5

Gln Glu Ser Ile Val Asp Ala Gly Pro Val Val Val His Cys Ser Ala
1               5                   10                  15

Gly Ile Gly Arg
            20

<210> SEQ ID NO 6
<211> LENGTH: 20
<212> TYPE: PRT
<213> ORGANISM: Artificial Sequence
<220> FEATURE:
<223> OTHER INFORMATION: IAN-labeled C463

<400> SEQUENCE: 6

Gln Glu Ser Ile Val Asp Ala Gly Pro Val Val Val His Cys Ser Ala
1               5                   10                  15

Gly Ile Gly Arg
            20
```